(12) United States Patent
Janssen et al.

(10) Patent No.: US 7,449,575 B2
(45) Date of Patent: Nov. 11, 2008

(54) SUBSTITUTED DIAMINO-1,3,5-TRIAZINE DERIVATIVES

(75) Inventors: Paul A. J. Janssen, Vosselaar (BE); Jan Heeres, Vosselaar (BE); Henri E. L. Moereels, Ekeren (BE); Michael Joseph Kukla, Spring House, PA (US); Donald W. Ludovici, Spring House, PA (US)

(73) Assignee: Janssen Pharmaceutica, Inc. (BE)

( * ) Notice: Subject to any disclaimer, the term of this patent is extended or adjusted under 35 U.S.C. 154(b) by 0 days.

(21) Appl. No.: 11/203,325

(22) Filed: Aug. 12, 2005

(65) Prior Publication Data

US 2006/0189614 A1     Aug. 24, 2006

Related U.S. Application Data

(60) Division of application No. 10/397,760, filed on Mar. 26, 2003, now Pat. No. 6,962,916, which is a division of application No. 10/002,456, filed on Nov. 15, 2001, now Pat. No. 6,858,609, which is a continuation of application No. 08/938,602, filed on Sep. 26, 1997, now Pat. No. 6,380,194.

(60) Provisional application No. 60/027,260, filed on Oct. 1, 1996.

(51) Int. Cl.
C07D 251/48     (2006.01)
C07D 403/04     (2006.01)

(52) U.S. Cl. .......................... 544/206; 544/207; 544/208

(58) Field of Classification Search .................. 544/206, 544/207, 208
See application file for complete search history.

(56) References Cited

U.S. PATENT DOCUMENTS

| | | | |
|---|---|---|---|
| 2,309,663 A | 2/1943 | Oldham | |
| 2,817,614 A | 12/1957 | Fraser | |
| 3,740,399 A | 6/1973 | Murai et al. | |
| 5,516,775 A | 5/1996 | Zimmerman et al. | |

FOREIGN PATENT DOCUMENTS

| | | |
|---|---|---|
| CA | 997762 | 9/1976 |
| DE | 2121694 | 11/1971 |
| DE | 2226474 | 2/1973 |
| EP | 588762 A1 | 3/1994 |
| EP | 834507 B1 | 5/2004 |
| GB | 771327 | 3/1957 |
| WO | WO 9310116 | 5/1993 |
| WO | WO 9510506 | 4/1995 |

OTHER PUBLICATIONS

Ludovici et al., Biorganic & Medicinal Chemistry Letters 11, 2229-2234, 2001.*
Chem. Abstracts, 10th Collective Chemical Substance Index, 1977-1981, 88:191532z.
Chem. Abstracts, 10th Collective Chemical Substance Index,, 1977-1981, 86:140514w.
Chem. Abstracts, 10th Collective Chemical Substance Index,, 1977-1981, 86:171887z.
Chem. Abstracts, 10th Collective Chemical Substance Index,, 1977-1981, 87:184445z.
Chem. Abstacts, 10th Collective Chemical Substance Index,, 1977-1981, 87:289:44281j.
Chem. Abstracts, 10th Collective Chemical Substance Index,, 1977-1981, 87:39869m.
Chem. Abstracts, 10th Collective Chemical Substance Index,, 1977-1981, 89:6595g.
Chem. Abstracts, 10th Collective Chemical Substance Index,, 1977-1981, 90:137776k.
Chem. Abstracts, 10th Collective Chemical Substance Index,, 1977-1981, 91:92058e.
Chem. Abstracts, 10th Collective Chemical Substance Index,, 1977-1981, 92:147448k.
Chem. Abstracts, 10th Collective Chemical Substance Index,, 1977-1981, 93:186300w.
Chem. Abstracts, 10th Collective Chemical Substance Index,, 1977-1981, 95:133399v.

(Continued)

Primary Examiner—Venkataraman Balasubramanian

(57) ABSTRACT

This invention concerns the compounds of formula

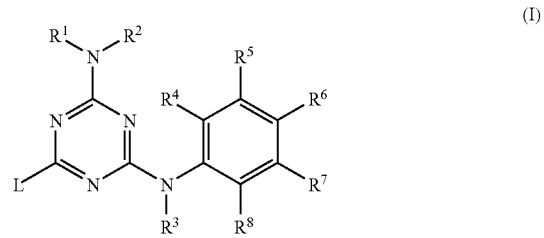

(I)

the pharmaceutically acceptable acid addition salts and the stereochemically isomeric forms thereof, wherein $R^1$ and $R^2$ are each independently selected from hydrogen; hydroxy; amino; optionally substituted $C_{1-6}$alkyl; $C_{1-6}$alkyloxy; $C_{1-6}$alkylcarbonyl; $C_{1-6}$alkyloxycarbonyl; $Ar^1$; mono- or di($C_{1-6}$alkyl)amino; mono- or di($C_{1-6}$alkyl)-aminocarbonyl; dihydro-2(3H)-furanone; or $R^1$ and $R^2$ taken together may form pyrrolidinyl, piperidinyl, morpholinyl, azido or mono- or di($C_{1-6}$alkyl)amino-$C_{1-4}$alkylidene; $R^3$ is hydrogen, $Ar^1$, $C_{1-6}$alkylcarbonyl, $C_{1-6}$alkyl, $C_{1-6}$alkyloxy-carbonyl, $C_{1-6}$alkyl substituted with $C_{1-6}$alkyloxycarbonyl; and $R^4$, $R^5$, $R^6$, $R^7$ and $R^8$ are each independently selected from hydrogen, halo, $C_{1-6}$alkyl, $C_{1-6}$alkyloxy, cyano, aminocarbonyl, nitro, amino, trihalomethyl or trihalomethyloxy; L is optionally substituted $C_{1-10}$alkyl; $C_{3-10}$alkenyl; $C_{3-10}$alkynyl; $C_{3-7}$cycloalkyl; $Ar^1$ is optionally substituted phenyl; for the manufacture of a medicine for the treatment of subjects suffering from HIV (Human Immunodeficiency Virus) infection. It further relates to new compounds being a subgroup of the compounds of formula (I), their preparation and compositions comprising them.

3 Claims, No Drawings

OTHER PUBLICATIONS

Chem. Abstracts, 11th Collective Chemical Substance Index, 1982-1986, 100:103930r.
Chem. Abstracts, 11th Collective Chemical Substance Index, 1982-1986, 100:103965f.
Chem. Abstracts, 11th Collective Chemical Substance Index, 1982-1986, 102:113990r.
Chem. Abstracts, 11th Collective Chemical Substance Index, 1982-1986, 104:19667a.
Chem. Abstracts, 11th Collective Chemical Substance Index, 1982-1986, 104:P 68890m.
Chem. Abstracts, 11th Collective Chemical Substance Index, 1982-1986, 105:227360c.
Chem. Abstracts, 11th Collective Chemical Substance Index, 1982-1986, 97:216812s.
Chem. Abstracts, 11th Collective Chemical Substance Index, 1982-1986, 99:23019w.
Chem. Abstracts, 12th Collective Chemical Substance Index, 1987-1991, 106:138773t.
Chem. Abstracts, 12th Collective Chemical Substance Index, 1987-1991, 106:214430w.
Chem. Abstracts, 12th Collective Chemical Substance Index, 1987-1991, 107:7699w.
Chem. Abstracts, 12th Collective Chemical Substance Index, 1987-1991, 108:P 169338a.
Chem. Abstracts, 12th Collective Chemical Substance Index, 1987-1991, 109:7035t.
Chem. Abstracts, 12th Collective Chemical Substance Index, 1987-1991, 110:213401h.
Chem. Abstracts, 12th Collective Chemical Substance Index, 1987-1991, 110:76120z.
Chem. Abstracts, 12th Collective Chemical Substance Index, 1987-1991, 110:95865n.
Chem. Abstracts, 12th Collective Chemical Substance Index, 1987-1991, 112:235928d.
Chem. Abstracts, 12th Collective Chemical Substance Index, 1987-1991, 113:132921n.
Chem. Abstracts, 12th Collective Chemical Substance Index, 1987-1991, 113:98073a.
Chem. Abstracts, 12th Collective Chemical Substance Index, 1987-1991, 114:101949u.
Chem. Abstracts, 12th Collective Chemical Substance Index, 1987-1991, 114:144083z.
Chem. Abstracts, 12th Collective Chemical Substance Index, 1987-1991, 114:62822a.
Chem. Abstracts, 12th Collective Chemical Substance Index, 1987-1991, 114:P 62949x.
Chem. Abstracts, 12th Collective Chemical Substance Index, 1987-1991, 115:159846v.
Chem. Abstracts, 12th Collective Chemical Substance Index, 1987-1991, 115:208741t.
Chem. Abstracts, 12th Collective Chemical Substance Index, 1987-1991, 115:P 183368m.
Chem. Abstracts, 13th Collective Chemical Substance Index, 1992-1996, 116:152491n.
Chem. Abstracts, 13th Collective Chemical Substance Index, 1992-1996, 116:174924h.
Chem. Abstracts, 13th Collective Chemical Substance Index, 1992-1996, 116:60382z.
Chem. Abstracts, 13th Collective Chemical Substance Index, 1992-1996, 117:151437h.
Chem. Abstracts, 13th Collective Chemical Substance Index, 1992-1996, 117:192379j.
Chem. Abstracts, 13th Collective Chemical Substance Index, 1992-1996, 117:251937q.
Chem. Abstracts, 13th Collective Chemical Substance Index, 1992-1996, 117:27277s.
Chem. Abstracts, 13th Collective Chemical Substance Index, 1992-1996, 118:P263477y.
Chem. Abstracts, 13th Collective Chemical Substance Index, 1992-1996, 120:322653u.
Chem. Abstracts, 13th Collective Chemical Substance Index, 1992-1996, 123:prP313998v.
Chem. Abstracts, 13th Collective Chemical Substance Index, 1992-1996, 124:pr 318043k.
Chem. Abstracts, 8th Collective Chemical Substance Index, 1967, 70:115608s.
Chem. Abstracts, 8th Collective Chemical Substance Index, 1967, 70:77919j.
Chem. Abstracts, 8th Collective Chemical Substance Index, 1967, 72:P 66952e.
Chem. Abstracts, 8th Collective Chemical Substance Index, 1967, 73:66940v.
Chem. Abstracts, 8th Collective Chemical Substance Index, 1967, 74:13108u.
Chem. Abstracts, 8th Collective Chemical Substance Index, 1967, 75:151765c.
Chem. Abstracts, 9th Collective Chemical Substance Index, 1972-1976, 76:60183r.
Chem. Abstracts, 9th Collective Chemical Substance Index, 1972-1976, 76:99624k.
Chem. Abstracts, 9th Collective Chemical Substance Index, 1972-1976, 76:P 85846x.
Chem. Abstracts, 9th Collective Chemical Substance Index, 1972-1976, 77:P 5536d.
Chem. Abstracts, 9th Collective Chemical Substance Index, 1972-1976, 78:154735r.
Chem. Abstracts, 9th Collective Chemical Substance Index, 1972-1976, 78:42629c.
Chem. Abstracts, 9th Collective Chemical Substance Index, 1972-1976, 78:85022a.
Chem. Abstracts, 9th Collective Chemical Substance Index, 1972-1976, 78:P 136344h.
Chem. Abstracts, 9th Collective Chemical Substance Index, 1972-1976, 78:P 159683g.
Chem. Abstracts, 9th Collective Chemical Substance Index, 1972-1976, 79:105207g.
Chem. Abstracts, 9th Collective Chemical Substance Index, 1972-1976, 79:53846t.
Chem. Abstracts, 9th Collective Chemical Substance Index, 1972-1976, 79:53846t.
Chem. Abstracts, 9th Collective Chemical Substance Index, 1972-1976, 79:53847u.
Chem. Abstracts, 9th Collective Chemical Substance Index, 1972-1976, 79:P 115635j.
Chem. Abstracts, 9th Collective Chemical Substance Index, 1972-1976, 80:82903k.
Chem. Abstracts, 9th Collective Chemical Substance Index, 1972-1976, 81:106050d.
Chem. Abstracts, 9th Collective Chemical Substance Index, 1972-1976, 81:64018s.
Chem. Abstracts, 9th Collective Chemical Substance Index, 1972-1976, 81:P 136188x.
Chem. Abstracts, 9th Collective Chemical Substance Index, 1972-1976, 81:P 82387r.
Chem. Abstracts, 9th Collective Chemical Substance Index, 1972-1976, 82:156832b.
Chem. Abstracts, 9th Collective Chemical Substance Index, 1972-1976, 82:170841k.
Chem. Abstracts, 9th Collective Chemical Substance Index, 1972-1976, 82:98508n.
Chem. Abstracts, 9th Collective Chemical Substance Index, 1972-1976, 83:37636b.
Chem. Abstracts, 9th Collective Chemical Substance Index, 1972-1976, 83:P 79289w.
Chem. Abstracts, 9th Collective Chemical Substance Index, 1972-1976, 84:31612g.
Chem. Abstracts, 9th Collective Chemical Substance Index, 1972-1976, 85:178061p.
Chem. Abstracts, 9th Collective Chemical Substance Index, 1972-1976, 85:78450w.
Chem. Abstracts, 9th Collective Chemical Substance Index, 1972-1976.
Chem. Abstracts, vol. 51, 13468a-d.

Furukawa, M. et al., Synthesis of compounds related to guanidine and their inhibitory action on growth of HeLa cells:, Chemical & Pharmaceutical Bulletin, vol. 9, 1961, pp. 914-921.

Shapiro, S. L. et al., "Guanamines V. Chioromethylguanamines", J. Org. Chem., vol. 26, 1961, pp. 68-74.

Subject Index, 11918s: 51P 15618b; 52:2870h55:18754b.

Subject Index, 12871s: 46:4024b, 49:3980e; 49:2446e; 48:9810f; 49:P668d; 50:P10447c; 49:39801; 49:2446f; 46:P 1461; 4024b.

Subject Index, 12872s: 49:3980h: 48:9810h; 44:7851; 47:1135e; 49:10316d; 41:5136e; 47:1135e; 48:1581h.

Subject Index, 12874: 46:8659i.

Subject Index, 9519: 37:P 3769, 38:P 3667, 40:5059.

Subject Index: 23220s: 58:837g, 64:20469f, 58:526a, 60:P 534f, 63:8892b, 56:11593b, 58:837g.

Subject Index: 23221s: 57:16618d.

European Search Report—Application EP 97 20 2917, Munich, Dec. 22, 1997.

Guioca, "New Substituted Triazines and Their Diuretic Activity", Ann. Pharm. Fr., 31:283-292 (1973). (English Abstract Provided).

Kelarev V.I. et al., "Synthesis of 2-Amino and 2,4- Diamino-sym-Triazines Containing Sterically Hindered Phenol Segments", Khim. Geterotsikl. Soedin., 1392-1397 (1987).

Kelarev V.I. et al., "Synthesis and Properties of sym-Triazines. 10 Synthesis of 2,4-Diamino-sym-Triazines Containing a Sterically Hindered Phenol Substituent", Khim. Geterotsikl. Soedin., 1395-1399 (1992).

Yuki Y. et al., "Polymerization of 2-amino-4-o-toluidino-6-vinyl-s-triazine", Kobunshi Kagaku, 26 : 141-147 (1969) (English Abstract Provided).

Kreutzberger, Alfred et al., "Analgesic Drugs. XI. Diacyl Derivatives of Butyroguanamine", Arch. Pharm. (Weinheim) 1986, 319, 275 (English Abstract Provided).

Webb R.L. et al., "Diphenyl Cyanocarbonimidate. A Versatile Synthon for the Construction of Heterocyclic Systems", J. Heterocyclic Chem., 19:1205-1206 (1982).

Matsumoto et al., "A Facile Synthesis 4-(Cyanomethyl)indoles and 4-(Ethoxycarbonyl-Methyl) Indoles From 5-Halo-4-Oxo-4,5,6,7-Tetrahydroindoles", Heterocycles, 24(11), 3157-3162 (1986).

Koyanagi et al., Selective Cytotoxicity of Aids Virus Infection Toward HTLV-1_Transformed Cell Lines , Int. J. Cancer, 36, 445-451, (1985).

Chemical Abstracts, vol. 109, No. 1 (1988) Abstract No. 6482, pp. 615.

Chemical Abstracts, vol. 119, No. 7 (1993) Abstract No. 72581, pp. 1062.

Subject Index, 1967: 23327-02-6.

Chem. Abstracts, 9th Collective Chemical Substance Index, 1972-1976, 78:85022s.

Bulletin of the Chemical Society of Japan, 1970, vol. 43, No. 7, pp. 123-2129.

Kambayashi et al,, "Anti-Infmammatory Action of an s-Triazine Derivative in Rats", Arzneimittel-Forschung, 1975, vol. 25, No. 2, pp. 230-231.

Skulan, T. W. et al., "Natriuretic and Antiglycogenic Activities of a Series of Symmetrical Triazine and Pteridine Derivatives", The Journal of Pharmacology and Experimental Therapeutics, 1965, vol. 148, No. 3, pp. 356-362.

Kobunshi Ronbunshu, 1978, vol. 35, No. 2, pp. 69-73.

* cited by examiner

SUBSTITUTED DIAMINO-1,3,5-TRIAZINE DERIVATIVES

This application is a divisional application of prior application U.S. Ser. No. 10/397,760, filed on Mar. 26, 2003, now U.S. Pat. No. 6,962,916; which is a divisional application of prior application U.S. Ser. No. 10/002,456, filed Nov. 15, 2001, now U.S. Pat. No. 6,858,609, which is a continuation of prior application U.S. Ser. No. 08/938,602, filed on Sept. 26, 1997, now U.S. Pat. No. 6,380,194, which claims priority form United States provisional application Ser. No. 60/027,260, filed Oct. 1, 1996, the contents of all of which are hereby incorporated by reference.

The present invention is concerned with novel compounds of formula (I) having HIV replication inhibiting properties. The invention further relates to methods for preparing such novel compounds, pharmaceutical compositions comprising said novel compounds as well as the use as a medicine of said compounds.

Compounds structurally related to the present novel compounds are disclosed in the prior art. DE-2,121,694, published on Nov. 25, 1971, discloses a number of s-triazines useful as anti-inflammatory, tranquillising, antiviral, antispasmodic, hypo-glycaemic, diuretic, and vasodilating agents, and for modifying adreno-cortico hormone secretion. DE-2,226,474, published on Feb. 22, 1973, discloses diamino-1,3, 5-triazine derivatives with hormone secretion-increasing activity, and anti-inflammatory effect. Substituted triazines having diuretic activity were published in Guioca, *Ann. Pharm. Fr.*, 31:283-292 (1973). A number of 2,4-diamino-triazines were prepared in Kelarev V. I. et al., *Khim. Geterotsikl. Soedin.*, 1392-1397 (1987) and Kelarev V. I. et al., *Khim. Geterotsikl. Soedin.*, 1395-1399 (1992). The preparation of 2-amino-4-benzyl-6-o-toluidino-s-triazine was described in Yuki Y. et al., *Kobunshi Kagaku*, 26: 141-147 (1969). The use of aralkylguanamines, in particular 2-amino-4-anilino-6-benzyl-s-triazine, for the manufacture of resins is disclosed in U.S. Pat. No. 2,817,614, granted Dec. 24, 1957.

Unexpectedly, it has now been found that the compounds of formula (I) effectively inhibit the replication of the Human Immunodeficiency Virus (HIV) and consequently may be useful for the treatment of individuals infected by HIV.

The present invention concerns the use of compounds of formula

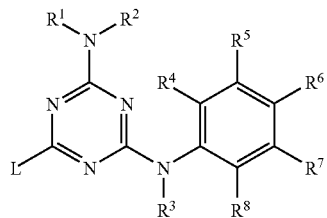

(I)

the pharmaceutically acceptable acid addition salts and the stereochemically isomeric forms thereof, wherein $R^1$ and $R^2$ are each independently selected from hydrogen; hydroxy; amino; $C_{1-6}$alkyl; $C_{1-6}$alkyloxy; $C_{1-6}$alkylcarbonyl; $C_{1-6}$alkyloxycarbonyl; $Ar^1$; mono- or di($C_{1-6}$alkyl)amino; mono- or di($C_{1-6}$alkyl)aminocarbonyl; dihydro-2 (3H)-furanone; $C_{1-6}$alkyl substituted with one or two substituents each independently selected from amino, imino, aminocarbonyl, aminocarbonylamino, hydroxy, hydroxy$C_{1-6}$alkyloxy, carboxyl, mono- or di($C_{1-6}$alkyl)amino, $C_{1-6}$alkyloxycarbonyl and thienyl; or $R^1$ and $R^2$ taken together may form pyrrolidinyl, piperidinyl, morpholinyl, azido or mono- or di($C_{1-6}$alkyl)amino$C_{1-4}$alkylidene;

$R^3$ is hydrogen, $Ar^1$, $C_{1-6}$alkylcarbonyl, $C_{1-6}$alkyl, $C_{1-6}$alkyloxycarbonyl, $C_{1-6}$alkyl substituted with $C_{1-6}$alkyloxycarbonyl; and $R^4$, $R^5$, $R^6$, $R^7$ and $R^8$ are each independently selected from hydrogen, hydroxy, halo, $C_{1-6}$alkyl, $C_{1-6}$alkyloxy, cyano, aminocarbonyl, nitro, amino, trihalomethyl or trihalomethyloxy;

L is $C_{1-10}$alkyl; $C_{3-10}$alkenyl; $C_{3-10}$alkynyl; $C_{3-7}$cycloalkyl; or L is $C_{1-10}$alkyl substituted with one or two substituents independently selected from $C_{3-7}$cycloalkyl; indolyl or indolyl substituted with one, two, three or four substituents each independently selected from halo, $C_{1-6}$alkyl, $C_{1-6}$alkyloxy, cyano, amino-carbonyl, nitro, amino, trihalomethyl, trihalomethyloxy, $C_{1-6}$alkylcarbonyl; phenyl or phenyl substituted with one, two, three, four or five substituents each independently selected from halo, hydroxy, $C_{1-6}$alkyl, $C_{1-6}$alkyloxy, cyano, aminocarbonyl, nitro, amino, trihalomethyl, trihalomethyloxy, $C_{1-6}$alkylcarbonyl; and, $Ar^1$ is phenyl, or phenyl substituted with one, two or three substituents each independently selected from halo, $C_{1-6}$alkyl, $C_{1-6}$alkyloxy, cyano, nitro or trifluoromethyl; for the manufacture of a medicine for the treatment of subjects suffering from HIV (Human Immunodeficiency Virus) infection.

This invention also concerns novel compounds of formula

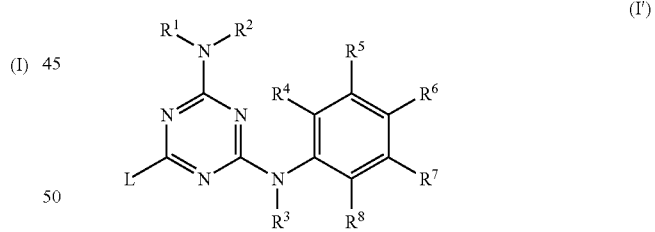

(I')

the pharmaceutically acceptable acid addition salts and the stereochemically isomeric forms thereof, wherein the substituents are as defined under formula (I); with the proviso that compounds (a) to (o)

| Co. No. | Alk | $R^1/R^2$ | $R^3$ | $R^4$ | $R^5$ | $R^6$ | $R^7$ | $R^8$ |
|---|---|---|---|---|---|---|---|---|
| a | 1-(4-(2-methylpropyl)phenyl)ethyl | H/H | H | $CH_3$ | H | H | H | H |
| b | 1-(4-(2-methylpropyl)phenyl)ethyl | H/H | H | H | H | $NO_2$ | H | H |
| c | 1-(4-(2-methylpropyl)phenyl)ethyl | H/H | $C_6H_5$ | H | H | H | H | H |
| d | 1-(4-(2-methylpropyl)phenyl)ethyl | H/H | H | $NO_2$ | H | $CH_3$ | H | H |

-continued

| Co. No. | Alk | $R^1/R^2$ | $R^3$ | $R^4$ | $R^5$ | $R^6$ | $R^7$ | $R^8$ |
|---|---|---|---|---|---|---|---|---|
| e | 1-(4-(2-methylpropyl)phenyl)ethyl | H/H | H | H | H | NH$_2$ | H | H |
| f | 4-(2-methylpropyl)phenylmethyl | H/H | H | H | CF$_3$ | H | H | H |
| g | 1-(4-(2-methylpropyl)phenyl)ethyl | H/H | H | H | H | Cl | H | H |
| h | 4-(2-methylpropyl)phenylmethyl | H/H | H | H | H | H | H | H |
| i | 3,4-dimethoxyphenylmethyl | H/H | H | H | H | H | H | H |
| j | 2,3-dimethoxyphenylmethyl | H/H | H | H | H | H | H | H |
| k | 3,4-diethoxyphenylmethyl | H/H | H | H | H | H | H | H |
| l | 2-(3,5-(1,1-dimethylethyl)-4-hydroxy-phenyl)ethyl | H/H | H | H | H | H | H | H |
| m | 2-(3,5-(1,1-dimethylethyl)-4-hydroxy-phenyl)ethyl | H/H | H | H | t-Bu | OH | t-Bu | H |
| n | phenylmethyl | H/H | H | CH$_3$ | H | H | H | H |
| o | phenylmethyl | H/H | H | H | H | H | H | H | are not included.

The proviso is intended to exclude compounds (a) to (f) disclosed in DE-2,121,694 and DE-2,226,474; compound (g) disclosed in DE-2,226,474; compounds (h) to (k) disclosed in Guioca, *Ann. Pharm. Fr.*, 31:283-292 (1973); compounds (l) disclosed in Kelarev V. I. et al., *Khim. Geterotsikl. Soedin.*, 1392-1397 (1987); compound (m) disclosed in Kelarev V. I. et al., *Khim. Geterotsikl. Soedin.*, 1395-1399 (1992); compound (n) disclosed in Yuki Y. et al., *Kobunshi Kagaku*, 26: 141-147 (1969); and compound (o) disclosed in U.S. Pat. No. 2,817,614.

As used in the foregoing definitions and hereinafter halo defines fluoro, chloro, bromo and iodo; $C_{1-2}$alkyl includes methyl and ethyl; $C_{1-3}$alkyl defines straight and branched chained saturated hydrocarbon radicals having from 1 to 3 carbon atoms such as, for example, methyl, ethyl, propyl and the like; $C_{1-4}$alkyl encompasses the straight and branched chained saturated hydrocarbon radicals as defined in $C_{1-3}$alkyl as well as the higher homologous thereof containing 4 carbon atoms such as, for example; butyl and the like; $C_{1-6}$alkyl encompasses the straight and branched chained saturated hydrocarbon radicals as defined in $C_{1-4}$alkyl as well as the higher homologues thereof containing 5 or 6 carbon atoms such as, for example pentyl or hexyl; $C_{3-6}$alkyl defines straight and branched chained saturated hydrocarbon radicals having from 3 to 6 carbon atoms such as, for example, propyl, butyl, pentyl, hexyl and the like; $C_{2-6}$alkyl encompasses the straight and branched chained saturated hydrocarbon radicals as defined in $C_{3-6}$alkyl as well as ethyl; $C_{1-10}$alkyl encompasses the straight and branched chained saturated hydrocarbon radicals as defined in $C_{1-6}$alkyl as well as the higher homologues thereof containing 7 to 10 carbon atoms such as, for example heptyl, octyl, nonyl or decyl; $C_{1-4}$alkylidene defines bivalent straight and branched chained hydrocarbons having from 1 to 4 carbon atoms such as, for example, methylene, ethylidene, propylidene, butylidene and the like; $C_{3-7}$cycloalkyl is generic to cyclopropyl, cyclobutyl, cyclopentyl, cyclohexyl and cycloheptyl; $C_{3-10}$alkenyl defines straight and branch chained hydrocarbon radicals containing one double bond and having from 3 to 10 carbon atoms such as, for example, 2-propenyl, 2-butenyl, 2-pentenyl, 3-pentenyl, 3-methyl-2-butenyl, 3-hexenyl, 3-heptenyl, 2-octenyl, 2-nonenyl, 2-decenyl and the like, whereby the carbon atom attached to the triazine ring is preferably an aliphatic carbon atom; $C_{3-10}$alkynyl defines straight and branch chained hydrocarbon radicals containing one triple bond and having from 3 to 10 carbon atoms such as, for example, 2-propynyl, 2-butynyl, 2-pentynyl, 3-pentynyl, 3-methyl-2-butynyl, 3-hexynyl, 3-heptynyl, 2-octynyl, 2-nonynyl, 2-decynyl and the like, whereby the carbon atom attached to the triazine ring is preferably an aliphatic carbon atom; $C_{1-6}$alkanediyl defines bivalent straight and branched chained saturated hydrocarbon radicals having from 1 to 6 carbon atoms, such as, for example, methylene, 1,2-ethanediyl, 1,3-propanediyl, 1,4-butanediyl, 1,5-pentanediyl, 1,6-hexanediyl and the branched isomers thereof.

The pharmaceutically acceptable acid addition salts as mentioned hereinabove are meant to comprise the therapeutically active non-toxic acid addition salt forms which the compounds of formula (I) or (I') are able to form. The compounds of formula (I) or (I') which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-amino-salicylic, pamoic and the like acids.

The term addition salts also comprises the hydrates and the solvent addition forms which the compounds of formula (I) or (I') are able to form. Examples of such forms are e.g. hydrates, alcoholates and the like.

The term stereochemically isomeric forms of compounds of formula (I) or (I'), as used hereinbefore, defines all possible compounds made up of the same atoms bonded by the same sequence of bonds but having different three-dimensional structures which are not interchangeable, which the compounds of formula (I) or (I') may possess. Unless other-wise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) or (I') both in pure form or in admixture with each other are intended to be embraced within the scope of the present invention.

Some of the compounds of formula (I) or (I') may also exist in their tautomeric forms. Such forms although not explicitly indicated in the above formula are intended to be included within the scope of the present invention.

Whenever used hereinafter, the term "compounds of formula (I) or (I')" is meant to include also the pharmaceutically acceptable acid addition salts and all stereoisomeric forms.

A special group of compounds are the compounds of formula (I-P) and include those compounds of formula (I) or (I') wherein $R^1$ and $R^2$ are each independently selected from hydrogen, $C_{1-6}$alkyl, $Ar^1$ or mono- or di($C_{1-6}$alkyl)aminocarbonyl; or $R^1$ and $R^2$ taken together may form pyrrolidinyl, piperidinyl or morpholinyl;

$R^3$ is hydrogen, $C_{1-6}$alkyl or $Ar^1$; and $Ar^1$ is phenyl, or phenyl substituted with 1, 2 or 3 substituents each independently selected from halo, $C_{1-6}$alkyl, $C_{1-6}$alkyloxy, cyano, nitro or trifluoromethyl; and L is a radical of formula

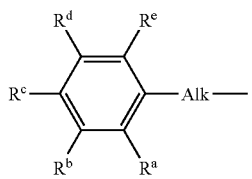

wherein Alk is $C_{1-6}$alkanediyl;

$R^a$, $R^b$, $R^c$, $R^d$, $R^e$, $R^4$, $R^5$, $R^6$, $R^7$ and $R^8$ are each independently selected from hydrogen, halo, $C_{1-6}$alkyl, $C_{1-6}$alkyloxy, cyano, aminocarbonyl, nitro, amino, trihalomethyl or trihalomethyloxy; or $R^a$ and $R^b$ taken together may form a bivalent radical of formula $$—CH=CH—NR^9— \quad (a\text{-}1),$$

$$—NR^9—CH=CH— \quad (a\text{-}2),$$

wherein $R^9$ is hydrogen or $C_{1-4}$alkyl.

Another special group of compounds are those compounds of formula (I-P) wherefrom the compounds (a) through (o) are excluded, said compounds being represented by formula (I'-P).

Interesting compounds are those compounds of formula (I') wherein $NR^1R^2$ is other than amino.

Other interesting compounds are those compounds of formula (I') wherein L is $C_{1-10}$alkyl; $C_{3-10}$alkenyl; $C_{3-10}$alkynyl; $C_{3-7}$cycloalkyl; or L is $C_{1-10}$alkyl substituted with one or two substituents independently selected from $C_{3-7}$cycloalkyl; indolyl or indolyl substituted with one, two, three or four substituents each independently selected from halo, $C_{1-6}$alkyl, $C_{1-6}$alkyloxy, cyano, aminocarbonyl, nitro, amino, trihalomethyl, trihalomethyloxy, $C_{1-6}$alkylcarbonyl; phenyl substituted with one, two, three, four or five substituents each independently selected from halo, $C_{1-3}$alkyl, $C_{3-6}$alkyloxy, cyano, aminocarbonyl, nitro, amino, trihalomethyl, trihalomethyloxy, $C_{1-6}$alkylcarbonyl.

Still other interesting compounds are those compounds of formula (I) wherein one of the following restrictions apply:

i) $R^4$ is hydroxy, halo, $C_{2-6}$alkyl, $C_{1-6}$alkyloxy, cyano, aminocarbonyl, amino, trihalomethyl or trihalomethyloxy; or ii) $R^5$ is hydroxy, halo, $C_{1-3}$alkyl, $C_{1-6}$alkyloxy, cyano, aminocarbonyl, nitro, amino, or trihalomethyloxy; or iii) $R^6$ is $C_{2-6}$alkyl, $C_{1-6}$alkyloxy, cyano, aminocarbonyl, nitro, trihalomethyl or trihalomethyloxy; or iv) $R^7$ is hydroxy, halo, $C_{1-3}$alkyl, $C_{1-6}$alkyloxy, cyano, aminocarbonyl, nitro, amino, trihalomethyl or trihalomethyloxy; or v) $R^8$ is hydroxy, halo, $C_{1-6}$alkyl, $C_{1-6}$alkyloxy, cyano, aminocarbonyl, nitro, amino, trihalomethyl or trihalomethyloxy.

Particular compounds are those compounds of formula (I) or (I') wherein L is $C_{3-10}$alkenyl or $C_{1-2}$alkyl substituted with one or two substituents independently selected from $C_{3-7}$cycloalkyl; indolyl or indolyl substituted with one, two, three or four substituents each independently selected from halo, $C_{1-6}$alkyl, $C_{1-6}$alkyloxy, cyano, aminocarbonyl, nitro, amino, trihalomethyl, trihalomethyloxy, $C_{1-6}$alkylcarbonyl; phenyl or phenyl substituted with one, two, three, four or five substituents each independently selected from halo, hydroxy, $C_{1-6}$alkyl, $C_{1-6}$alkyloxy, cyano, amino-carbonyl, nitro, amino, trihalomethyl, trihalomethyloxy, $C_{1-6}$alkylcarbonyl; more in particular, wherein L is $C_{5-8}$alkenyl or $C_{1-2}$alkyl substituted with one or two substituents independently selected from cyclopropyl; indolyl or indolyl substituted with halo; phenyl or phenyl substituted with one, two, three, four or five substituents each independently selected from halo, hydroxy, $C_{1-6}$alkyl, $C_{1-6}$alkyloxy, trihalomethyl, trihalomethyloxy, $C_{1-6}$alkylcarbonyl.

Also particular compounds are those compounds of formula (I) or (I') wherein $R^4$, $R^7$ and $R^8$ are hydrogen and $R^5$ and $R^6$ each independently are hydrogen, cyano, halo or aminocarbonyl; more in particular, wherein $R^4$, $R^5$, $R^7$ and $R^8$ are hydrogen and $R^6$ is cyano.

Other particular compounds are those compounds of formula (I) or (I') wherein $R^1$ and $R^2$ are each independently selected from hydrogen; hydroxy; amino; $C_{1-6}$alkyl; $C_{1-6}$alkyloxy; $C_{1-6}$alkylcarbonyl; $C_{1-6}$alkyloxycarbonyl; $Ar^1$; mono- or di($C_{1-6}$alkyl)-aminocarbonyl; dihydro-2(3H)-furanone; $C_{1-6}$alkyl substituted with one or two substituents each independently selected from amino, imino, aminocarbonyl, amino-carbonylamino, hydroxy, hydroxy$C_{1-6}$alkyloxy, carboxyl, mono- or di($C_{1-6}$alkyl)amino, $C_{1-6}$alkyloxycarbonyl and thienyl; or $R^1$ and $R^2$ taken together form azido or mono- or di($C_{1-6}$alkyl)amino$C_{1-4}$alkylidene; more in particular wherein $R^1$ is hydrogen and $R^2$ is hydrogen; hydroxy; amino; $C_{1-6}$alkyl; $C_{1-6}$alkyloxy; $C_{1-6}$alkylcarbonyl; $C_{1-6}$alkyloxycarbonyl; $Ar^1$; mono- or di($C_{1-6}$alkyl)aminocarbonyl; dihydro-2(3H)-furanone; $C_{1-6}$alkyl substituted with one or two substituents each independently selected from amino, imino, aminocarbonyl, aminocarbonylamino, hydroxy, hydroxy$C_{1-6}$alkyloxy, carboxyl, mono- or di($C_{1-6}$alkyl)amino, $C_{1-6}$alkyloxycarbonyl or thienyl.

A preferred group of compounds are those compounds of formula (I) or (I') wherein L is 2,6-dichlorophenylmethyl.

Another preferred group of compounds are those compounds of formula (I) or (I') wherein $R^3$ is hydrogen, $R^4$, $R^5$, $R^7$ and $R^8$ are hydrogen and $R^6$ is cyano.

Yet another group of preferred compounds are those compounds of formula (I) or (I') wherein $R^1$ is hydrogen and $R^2$ is hydrogen or hyroxy.

More preferred are those compounds or formula (I) or (I') wherein L is 2,6-dichloro-phenylmethyl, $R^3$ is hydrogen, $R^4$, $R^5$, $R^7$ and $R^8$ are hydrogen and $R^6$ is cyano.

Most preferred compounds are

4-[[4-amino-6-[(2,6-dichlorophenyl)methyl]-1,3,5-triazin-2-yl]amino]benzonitrile; 4-[[4-[(2,6-dichlorophenyl)methyl]-6-(hydroxyamino)-1,3,5-triazin-2-yl]amino]-benzonitrile and the pharmaceutically acceptable acid addition salts thereof.

In general, compounds of formula (I) can be made according to the methods described in DE-2,121,694, DE-2,226,474 and Guioca, *Ann. Pharm. Fr.*, 31:283-292 (1973).

The compounds of formula (I-a), being compounds of formula (I) wherein $R^1$ and $R^2$ are hydrogen, can be prepared by reacting an intermediate of formula (II) with an intermediate of formula (III) in a reaction-inert solvent such as, e.g. N,N-dimethylformamide.

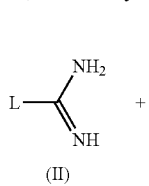

(II)

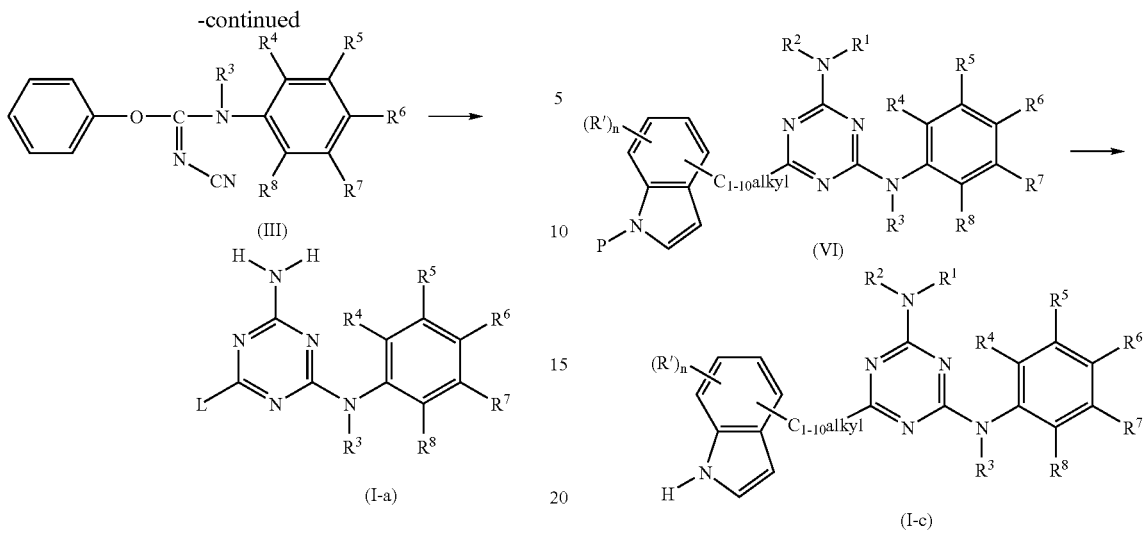

(III)

(I-a)

Compounds of formula (I-b), being compounds of formula (I) wherein $R^3$ is hydrogen, can be prepared by reacting an intermediate of formula (IV) with an intermediate of formula (V) in a reaction-inert solvent such as, e.g. N,N-dimethylformamide.

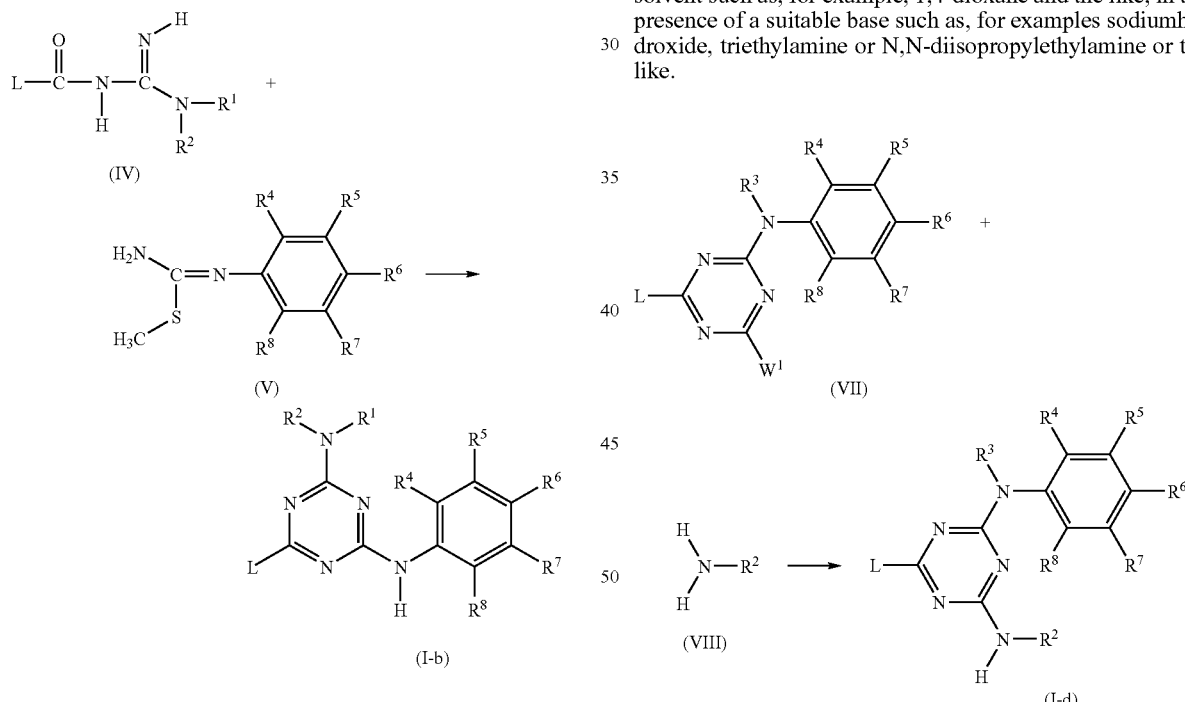

(IV)

(V)

(I-b)

Compounds of formula (I) wherein L is $C_{1-10}$alkyl substituted with indolyl or indolyl substituted with one, two, three or four substituents each independently selected from halo, $C_{1-6}$alkyl, $C_{1-6}$alkyloxy, cyano, aminocarbonyl, nitro, amino, trihalomethyl, trihalomethyloxy, $C_{1-6}$alkylcarbonyl, said substituents being represented by $(R')_n$ whereby n is 1 to 4 and said compounds being represented by formula (I-c), may be prepared by deprotecting an intermediate of formula (VI) wherein P is a suitable protecting group such as, for example, a toluenesulfonyloxy group or the like, according to art-known deprotection techniques such as refluxing in a reaction-inert solvent, e.g. water, methanol or a mixture thereof, in the presence of a base, e.g. potassium carbonate or the like.

(VI)

(I-c)

Compounds of formula (I) wherein $R^1$ is hydrogen, said compounds being represented by formula (I-d), can be prepared by reacting an intermediate of formula (VII) wherein $W^1$ is a suitable leaving group such as, for example, a halogen, with an amino derivative of formula (VIII) in a reaction inert solvent such as, for example, 1,4-dioxane and the like, in the presence of a suitable base such as, for examples sodiumhydroxide, triethylamine or N,N-diisopropylethylamine or the like.

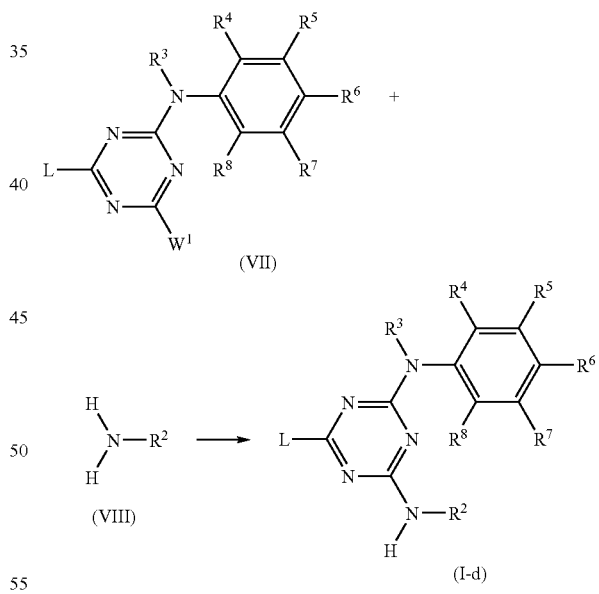

(VII)

(VIII)

(I-d)

In case $R^2$ contains a hydroxy moiety, it may be convenient to perform the above reaction with a protected form of intermediate (VIII) whereby the hydroxy moiety bears a suitable protecting group P being, for instance, a trialkylsilyl group, and subsequently removing the protective group according to art-known methodologies.

Compounds of formula (I) whereby $R^1$ and $R^3$ are hydrogen and $R^2$ and the $C_6(R^4R^5R^6R^7R^8)$ moiety are identical, said compounds being represented by formula (I-e), may be prepared by reacting an intermediate of formula (IX) wherein $W^2$ is a suitable leaving group such as, for example, a halogen or the like, with an intermediate of formula (X) in a reaction inert solvent such as, for example, 1,4-dioxane.

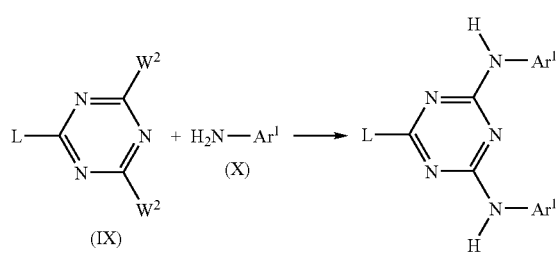

(I-e)

Compounds of formula (I) wherein $R^1$ and $R^2$ are other than hydrogen and are being represented by $R^{1'}$ and $R^{2'}$ respectively, said compounds being represented by formula (I-f-1), can be prepared by reacting an intermediate of formula (XI) with an intermediate of formula (XII) wherein $W^3$ is a suitable leaving group such as, for example, a halogen, in a reaction-inert solvent such as, for example, N,N-dimethylformamide or N,N-dimethylacetamide, and in the presence of a suitable base such as, for example, sodium hydride or potassium carbonate.

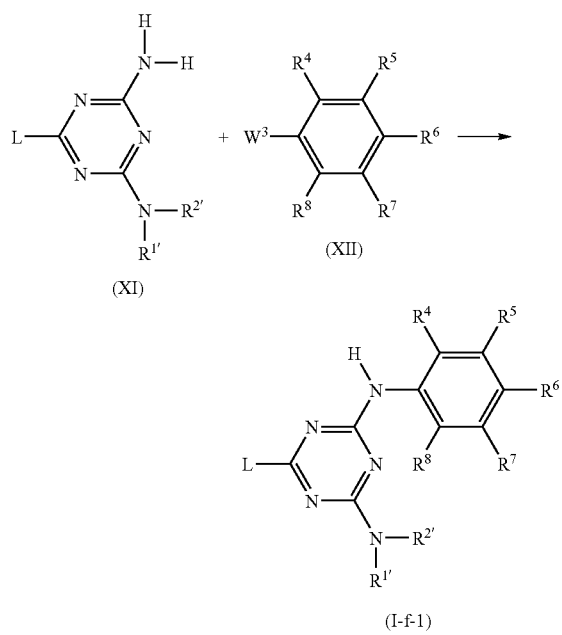

In case intermediate (XII) is limited to $W^3$—$Ar^1$ (XII-b) and $R^3$ is hydrogen, the reaction time may be adjusted to form the disubstituted analogues being represented by formula (I-f-2).

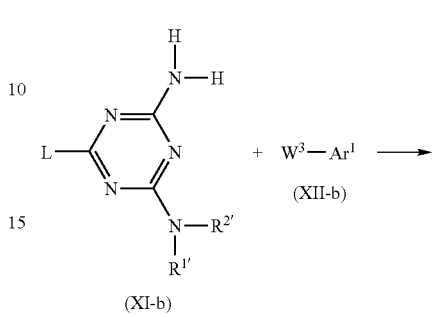

(XI-b)

(I-f-2)

The compounds of formula (I) may further be prepared by converting compounds of formula (I) into each other according to art-known group transformation reactions.

For instance, compounds of formula (I-a) may be reacted with an anhydride of formula (XIII) wherein R is defined such that —C(=O)—R is part of the definition of $R^1$ or $R^2$, according to the method described in Arch. Pharm. (Waldheim) 1986, 319, 275, thus forming compounds of formula (I-g). In this reaction, the reflux time is critical; longer times led to lower yield of the monosubstituted endproducts and increased formation of di- and where possible, trisubstituted endproducts.

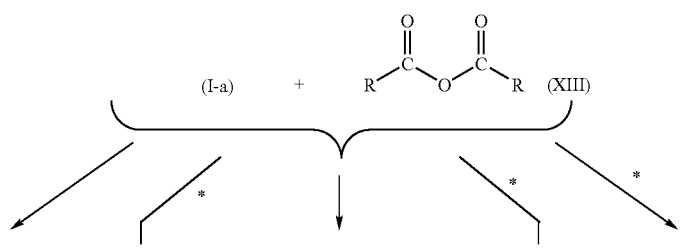

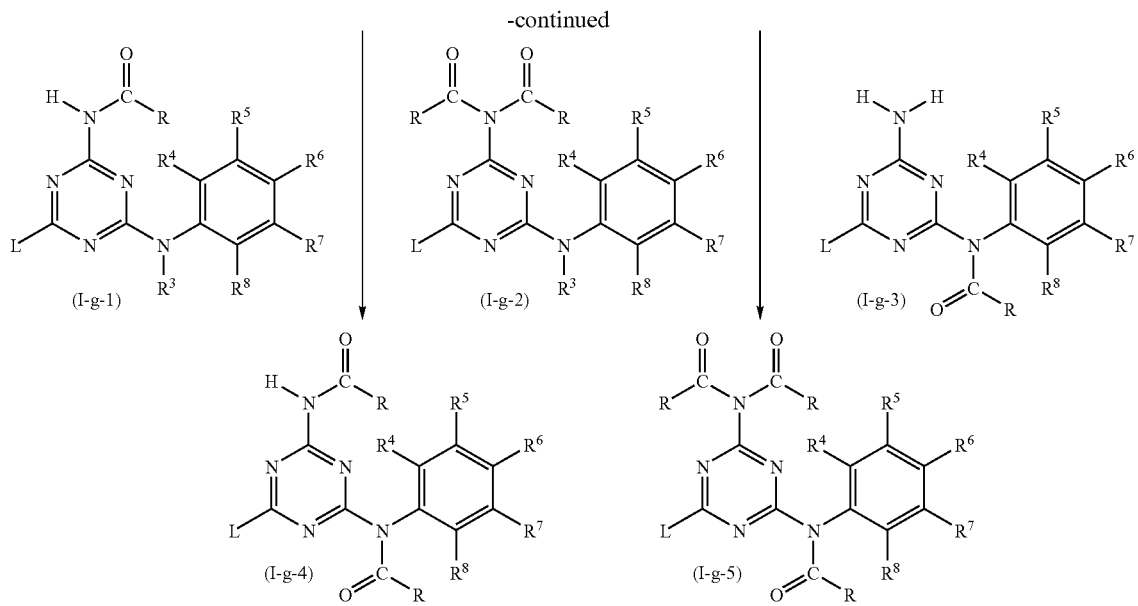

*only in case $R^3$ is hydrogen

Compounds of formula (I-a) can also be reacted with a reagent of formula (XIV) in a reaction-inert solvent such as, for example, N,N-dimethylformamide, in the presence of a base such as, for example, sodium hydride.

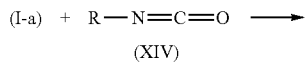

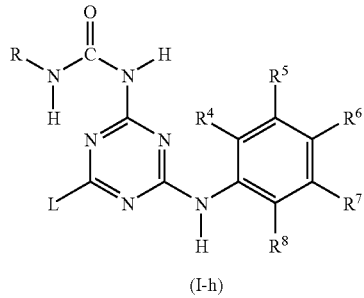

Some of the intermediates as mentioned hereinabove are commercially available or can be prepared according to art-known procedures, while other intermediates are deemed novel.

Intermediates of formula (II) can be prepared by reacting a cyano derivative of formula (XV) with ammonium chloride (XVI) or a functional derivative thereof in a reaction-inert solvent such as, for example, toluene, and in the presence of a suitable catalyst such as, for example, trimethylaluminium.

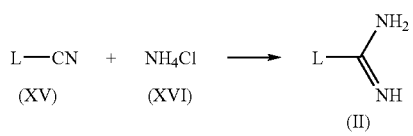

Intermediates of formula (III) can generally be made by reacting diphenyl N-cyano-carbonimidate of formula (XVII), which can be prepared according to Webb R. L. et al., *J. Heterocyclic Chem.*, 19:1205-1206 (1982), with an aniline derivative of formula (XVIII) in a reaction-inert solvent such as, e.g. N,N-dimethylformamide.

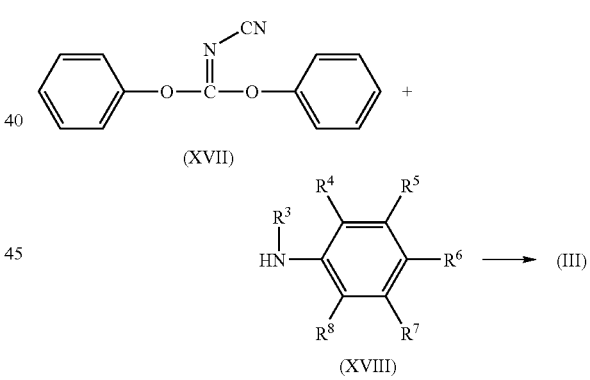

Intermediates of formula (VII) can be prepared by first making a Grignard reagent of an intermediate of formula (XIX) wherein $W^4$ is a suitable leaving group such as, for example, a halogen, e.g. bromine, in the presence of magnesium in a reaction-inert solvent such as, for example, diethyl ether, and subsequently reacting said Grignard reagent with an intermediate of formula (XX) wherein $W^5$ is a suitable leaving group such as, for example, a halogen, e.g. chlorine, in a reaction-inert solvent such as, for example, benzene, thus forming an intermediate of formula (XXI). It may be convenient to perform the above reaction under a inert-atmosphere such as, for instance, argon. Intermediate (XXI) may be isolated from its reaction medium, or may be in situ further reacted with an intermediate of formula (XXII) in a reaction-inert solvent such as, for example, 1,4-dioxane, and in the presence of a suitable base such as, for example, diisopropylethaneamine or the like, thus forming an intermediate of formula (VII). The intermediates of formula (VII) are deemed novel.

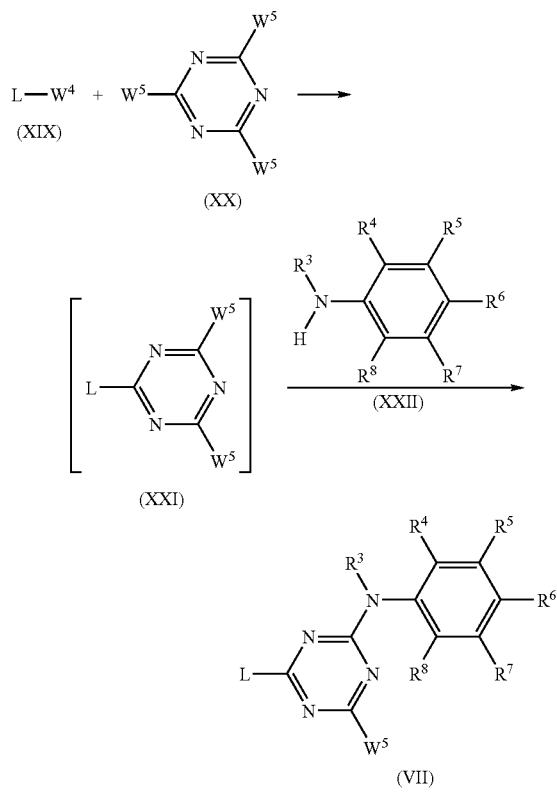

Intermediates of formula (XI) can be prepared by reacting an intermediate of formula (XXIII) with an intermediate of formula (XXIV) in a reaction-inert solvent such as, for example, N,N-dimethylformamide.

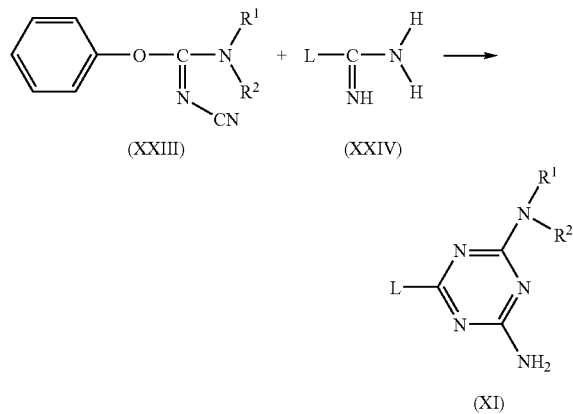

Compounds of formula (I) and some of the intermediates may have one or more stereogenic centers in their structure, present in a R or a S configuration.

The compounds of formula (I) as prepared in the hereinabove described processes may be synthesized as a mixture of stereoisomeric forms, in particular in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I) show antiretroviral properties, in particular against Human Immunodeficiency Virus (HIV), which is the aetiological agent of Acquired Immune Deficiency Syndrome (AIDS) in humans. The HIV virus preferentially infects human T-4 cells and destroys them or changes their normal function, particularly the coordination of the immune system. As a result, an infected patient has an everdecreasing number of T-4 cells, which moreover behave abnormally. Hence, the immunological defense system is unable to combat infections and neoplasms and the HIV infected subject usually dies by opportunistic infections such as pneumonia, or by cancers. Other conditions associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC).

The present compounds also show activity against HIV-1 strains that have acquired resistance to art-known non-nucleoside reverse transcriptase inhibitors. They also have little or no binding affinity to human α-1 acid glycoprotein.

Due to their antiretroviral properties, particularly their anti-HIV properties, especially their anti-HIV-1-activity, the compounds of formula (I), their pharmaceutically acceptable salts and the stereochemically isomeric forms thereof, are useful in the treatment of individuals infected by HIV and for the prophylaxis of these individuals. In general, the compounds of the present invention may be useful in the treatment of warm-blooded animals infected with viruses whose existence is mediated by, or depends upon, the enzyme reverse transcriptase. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic CNS diseases caused by retroviruses, such as, for example HIV mediated dementia and multiple sclerosis.

The compounds of the present invention therefore may be used as medicines against above-mentioned conditions. Said use as a medicine or method of treatment comprises the systemic administration to HIV-infected subjects of an amount effective to combat the conditions associated with HIV and other pathogenic retroviruses, especially HIV-1.

The subject compounds may be formulated into various pharmaceutical forms for administration purposes. Said pharmaceutical forms or compositions are deemed novel and consequently constitute another aspect of the present invention. Also the preparation of said compositions constitutes a further aspect of the present invention. As appropriate compositions there may be cited all compositions usually employed for systemically administering drugs. To prepare the pharmaceutical compositions of this invention, an effective amount of the particular compound, optionally in acid addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

It is especially advantageous to formulate the aforementioned pharmaceutical compositions in dosage unit form for ease of administration and uniformity of dosage. Dosage unit form as used herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions and the like, and segregated multiples thereof.

Those of skill in the treatment of HIV-infection could determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines and are not intended to limit the scope or use of the invention to any extent.

Also, the combination of an antiretroviral compound and a compound of formula (I) can be used as a medicine. Thus, the present invention also relates to a product containing (a) a compound of formula (I), and (b) another antiretroviral compound, as a combined preparation for simultaneous, separate or sequential use in anti-HIV treatment. The different drugs may be combined in a single preparation together with pharmaceutically acceptable carriers. Said other antiretroviral compounds may be known antiretroviral compounds such as nucleoside reverse transcriptase inhibitors, e.g. zidovudine (3'-azido-3'-deoxythymidine, AZT), didanosine (dideoxy inosine; ddI), zalcitabine (dideoxycytidine, ddC) or lamnivudine (3'-thia-2'-3'-dideoxycytidine, 3TC) and the like; non-nucleoside reverse transcriptase inhibitors such as suramine, pentamidine, thymopentin, castanospermine, dextran (dextran sulfate), foscarnet-sodium (trisodium phosphono formate), nevirapine (11-cyclopropyl-5,11-dihydro-4-methyl-6H-dipyrido[3,2-b: 2',3'-e][1,4]diazepin-6-one), tacrine (tetrahydro-aminoacridine) and the like; compounds of the TIBO (tetrahydro-imidazo[4,5,1-jk][1,4)-benzodiazepine-2 (1H)-one and thione)-type e.g. (S)-8-chloro-4,5,6,7-tetrahydro-5-methyl-6-(3-methyl-2-butenyl)imidazo-[4,5,1-jk][1,4]benzodiazepine-2(1H)-thione; compounds of the α-APA (α-anilino phenyl acetamide) type e.g. α-[(2-nitro-phenyl) amino]-2,6-dichlorobenzene-acetamide and the like; TAT-inhibitors, e.g. RO-5-3335 and the like; protease inhibitors e.g. indinavir, ritanovir, saquinovir and the like; or immunomodulating agents, e.g. levamisole and the like.

The following examples are intended to illustrate and not to limit the scope of the present invention.

Experimental Part

Hereinafter "RT" means room temperature, "DCM" means dichloromethane, "DMF" means N,N-dimethylformamide and "ACN" means acetonitrile.

A. Preparation of the Intermediates

EXAMPLE A.1 a) A mixture of 4-cyano-aniline (2.48 g) and diphenyl N-cyano-carbonimidate (5.0 g) in DMF (25 ml) was stirred for 20 hours at 110° C. under argon flow. Water was added and the resulting precipitate was filtered off, to give a brownish solid. This fraction was recrystallized from ACN. The precipitate was filtered off and dried, yielding 1.67 g (30%) of phenyl N'-cyano-N-(4-cyanophenyl)carbamimidate (intermediate 1). In a similar way, phenyl N'-cyano-N-(3-cyanophenyl)carbamimidate (intermediate 2); phenyl N'-cyano-N-(4-chlorophenyl)carbamimidate (intermediate 3) and 6-phenyl N'-cyano-N,N-dimethylcarbaimidate (intermediate 7) were prepared.

b) A mixture of intermediate (7) (0.01746 mol) and 2,6-dichloro-benzene-ethanimidamide (0.01746 mol) in DMF (30 ml) was stirred for 24 hours at 85° C. After cooling, the reaction mixture was quenched with H$_2$O and the precipitate was filtered off and dried, yielding 5.00 g (96.0%) of 6-[(2, 6-dichlorophenyl)methyl]-N-2-dimethyl-1,3,5-triazine-2,4-diamine (intermediate 31).

EXAMPLE A.2 a) A mixture of NH₄Cl (2.55 g) in toluene (100 ml) was stirred and cooled in an ice bath under argon flow. Al(CH₃)₃/ toluene (23.9 ml; 2.0 M) was added and the resulting mixture was stirred for 1.5 hours at RT. 5-Chloro-1-[(4-methylphenyl)-sulfonyl]-1H-indole-4-acetonitrile, which can be prepared according to Matsumoto et al., *Heterocycles*, 24(11), 3157-3162 (1986), (3.0 g) was added and the reaction mixture was stirred for 24 hours at 80° C. Then, the reaction mixture was poured into a slurry of 96 g of silica gel in DCM (200 ml), stirred, filtered, and the filter cake was washed with methanol (400 ml), and evaporated to give 5.35 g of white solid. The solid was dissolved in DCM, washed with 3 N NaOH, dried with potassium carbonate, filtered, and the filtrate was evaporated, yielding 2.80 g (89%, white solid) of 5-chloro-1-[(4-methylphenyl)sulfonyl]-1H-indole-4-ethanimidamide (intermediate 4).

b) A mixture of intermediate (4) (2.61 g) and intermediate (1) (1.89 g) in DMF (25 ml) was stirred for 24 hours at 65° C. under argon flow. Water was slowly added and the precipitate filtered to give 3.55 g of an off-white solid. The solid was stirred in refluxing ACN, cooled and filtered to give 2.54 g (66%) of white solid. A 0.30 g sample was recrystallized in methanol. The precipitate was filtered off and dried, yielding 0.28 g (62%, white solid) of 4-[[4-amino-6-[(4-cyanophenyl)amino]-1,3,5-triazin-2-yl]methyl]-5-chloro-1-[(4-methylphenyl)sulfonyl]-1H-indole (intermediate 5).

Table 1 lists intermediates which were prepared according to the procedure described in example A.2a.

TABLE 1

$$R^b\underset{NH}{\overset{R^a}{-}}\overset{}{C}-NH_2$$

| Interm No. | $R^a$ | $R^b$ |
|---|---|---|
| 8 | H | 3-methoxyphenyl |
| 9 | H | 3-ethoxyphenyl |
| 10 | H | 3,5-dimethylphenyl |
| 11 | H | 2,3-dimethoxyphenyl |
| 12 | H | 2,5-difluorophenyl |
| 13 | H | 2,3,6-trifluorophenyl |
| 14 | H | 3,5-dimethoxyphenyl |
| 15 | H | 2,3,5,6-tetramethylphenyl |
| 16 | H | 3,5-(trifluoromethyl)-phenyl |
| 17 | H | 2-fluoro-6-(trifluoromethyl)-phenyl |
| 18 | H | 3,5-difluorophenyl |
| 19 | H | 2-methoxy-5-(methylcarbonyl)-phenyl |
| 20 | H | CH₂—CH=C(CH₃)₂ |
| 21 | H | CH=C(CH₃)₂ |
| 22 | H | CH₂—CH=C(C₂H₅)₂ |
| 23 | H | 2,3,6-trichlorophenyl |
| 24 | 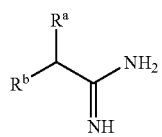 | 2,6-dichlorophenyl |
| 25 | H | 3-(trifluoromethoxy)-phenyl |
| 26 | H | 2,5-dimethoxy-phenyl |

EXAMPLE A.3

Iodomethane (1.76 ml) was added to 4-cyanophenyl-thiourea (5.0 g) in acetone (100 ml). The reaction mixture was stirred overnight at RT. The precipitate was filtered off, dried and dissolved in DCM. The organic solution was washed with NH₃ (aq.) (excess), dried with potassium carbonate, filtered, and the solvent was evaporated, yielding 4.53 g (84%, white solid) of methyl N'-(4-cyanophenyl)-carbamimidothioate (intermediate 6).

EXAMPLE A.4 a) A solution of 2-(bromomethyl)-1,3-dichlorobenzene (about 10% of 0.383 mol) in diethylether (240 ml) was added to magnesium (0.383 mol) in diethylether (240 ml) under argon. Once the reaction started, the remainder of 2-(bromomethyl)-1,3-dichlorobenzene in diethylether was added. The solution was stirred at RT for 2.5 hours and then added via canula to a solution of 2,4,6-trichloro-1,3,5-triazine (0.319 mol) in benzene (480 ml) while keeping the temperature below 15° C. The reaction mixture was stirred for one hour in an ice bath, then for 2 hours at RT. A solution of 4-amino-benzonitrile (0.351 mol) in N,N-diisopropylethylamine (61.0 ml) and 1,4-dioxane (500 ml) was added and the reaction mixture was stirred at RT for 40 hours. The solvent was evaporated. Water and ethylacetate were added. The solution was stirred, then the solid was filtered off, washed with ethylacetate and water, yielding 129.9 g of 4-[[4-chloro-6-[(2,6-dichlorophenyl)methyl]-1,3,5-triazin-2-yl]-amino] benzonitrile (intermediate 27; mp. 243-244° C.).

In a similar way, 4-[[4-chloro-6-[(2,4-dichlorophenyl)methyl]-1,3,5-triazin-2-yl]amino]benzonitrile (intermediate 28) and 4-[[4-chloro-6-[(2-chlorophenyl)methyl]-1,3,5-triazin-2-yl]amino]benzonitrile (intermediate 29) were prepared.

b) 2,4-dichloro-6-[(2,6-dichlorophenyl)methyl]-1,3,5-triazine (intermediate 30) was prepared according to the procedure described in example A.4a but was stopped prior to the addition of 4-aminobenzonitrile

B. Preparation of the Final Compounds

EXAMPLE B.1 a) Intermediate (1) (1.66 g) was added to a solution of 2,6-dichlorobenzene-ethanimidamide (1.29 g) in DMF (13 ml). The reaction mixture was stirred for three days at RT, then for two days at 60° C. under argon flow. Water was added and the precipitate was filtered off. This fraction was refluxed in ACN (500 ml), cooled and the precipitate was filtered off and dried, yielding 1.58 g (67%, white solid) of 4-[[4-amino-6-[(2,6-dichlorophenyl)methyl]-1,3,5-triazin-2-yl]amino] benzonitrile (compound 1).

b) Compound (1) (0.00135 mol) and acetic acid anhydride (20 ml) were combined and heated to reflux for 10 minutes. The reaction mixture was then removed from the oil bath and cooled to RT. The precipitate was filtered off, yielding 0.25 g (45%) of N-(4-[(4-cyanophenyl)amino]-6-[(2,6-dichlorophenyl)methyl]-1,3,5-triazin-2-yl]-acetamide (compound 22).

An increase of the time of reflux led to the disubstituted (compound 40) and the trisubstituted (compound 41) analogue of compound 22.

EXAMPLE B.2

Methanol (120 ml) was added to a mixture of intermediate (5) (2.35 g) and K$_2$CO$_3$ (9.19 g) in water (40 ml). The resulting reaction mixture was stirred and refluxed for 19 hours under argon. Water (120 ml) was added, the precipitate was filtered off and purified by column chromatography over silica gel (eluent: DCM/2-propanone 90/10). Two desired fractions were collected and their solvent was evaporated. The first fraction group was slurried in ACN, cooled, filtered off and dried, yielding 0.75 g (45%, white solid) of 4-[[4-amino-6-[(5-chloro-1H-indol-4-yl)methyl]-1,3,5-triazin-2-yl]amino]benzonitrile (compound 8, mp. 267-268° C.). The second column fraction group yielded 0.15 g of 4-[[4-amino-6-[(5-chloro-1H-indol-4-yl)methyl]-1,3,5-triazin-2-yl]amino]benzamide (compound 9). After 24 hours at RT the aqueous filtrate was filtered to give 0.25 g of compound (9). The two fractions of compound 9 were combined, dissolved in 500 ml of refluxing methanol, hot filtered, the filtrate concentrated to 50 ml, cooled and filtered, then dried, yielding 0.25 g (14%) of 4-[[4-amino-6-[(5-chloro-1H-indol-4-yl) methyl]-1,3,5-triazin-2-yl]amino]benzamide (compound 9, mp. 204-205° C.).

EXAMPLE B.3

A mixture of compound (1) (1.0 g) and sodium hydride (0.11 g), in DMF (20 ml) was stirred for 20 minutes at RT under argon flow. Then, 2-isocyanato-propane (0.27 ml) was added dropwise over 30 minutes and the reaction mixture was allowed to stir at RT overnight. The solvent was evaporated and water added. The residue was filtered, washed with water and diethyl ether, and recrystallized from 1,4-dioxane. The precipitate was filtered off and dried, yielding 0.95 g (85.1%) of N-[4-[(4-cyano-phenyl)amino]-6-[(2,6-dichlorophenyl) methyl]-1,3,5-triazin-2-yl]-N'-(1-methylethyl)-urea (compound 6, mp. 267-268° C.).

EXAMPLE B.4

A mixture of N-[amino(methylamino)methyl]-2,6-dichloro-benzeneacetamide (4.15 g) and intermediate 6 (3.05 g) in DMF (25 ml) was stirred and refluxed for 20 hours. The solvent was evaporated, the residue dissolved in DMF (25 ml) and heated at 80° C. for 16 hours and at 100-108° C. for another 66 hours. The reaction mixture was cooled, quenched with water, extracted with diethyl ether, and washed with dilute NaOH, water, brine, and dried over K$_2$CO$_3$. The solvent was evaporated, and the residue was purified by flash column chromatography, and recrystallized from 2-propanol, and finally from methanol, yielding 0.78 g (12.6%) of 4-[[4-[(2,6-dichlorophenyl)methyl]-6-(methyl-amino)-1,3,5-triazin-2-yl]amino]benzonitrile (compound 7, mp. 229-230° C.).

EXAMPLE B.5 a) Intermediate (27) (0.00423 mol), 2-amino-acetamide (0.00431 mol), 1,4-dioxane (20 ml) and N,N-diisopropyl-ethylamine (0.00862 mol) were combined and stirred at RT for 16 hours under argon. The reaction mixture was quenched with H$_2$O and filtered. The residue was washed with H$_2$O, filtered and recrystallized from ACN (200 ml). The precipitate was filtered off and dried, yielding 0.75 g (41.4%) of [N-[4-[(4-cyano-phenyl)amino]-6-[(2,6-dichlorophenyl)methyl]-1,3,5-triazin-2-yl]]aminoacetamide (compound 14).

b) 4-[[4-[(2,6-dichlorophenyl)methyl]-6-hydrazino-1,3,5-triazin-2yl]amino]benzonitrile (compound 15) was prepared in a similar manner as described in example B.5a, but N,N-diisopropylethylamine was not used.

EXAMPLE B.6 a) Intermediate (27) (0.0128 mol), 1,4-dioxane (50 ml), and O-(trimethylsilyl)hydroxyl-amine, (0.134 mol) were combined under argon. The reaction mixture was stirred at RT for 20 hours. The reaction mixture was concentrated and DCM (50 ml), NaOH (1 N; 50 ml), and HCl (1N; 100 ml) were added. The solution was stirred for one hour. The precipitate was filtered off and recrystallized from methanol. The precipitate was filtered off and dried, yielding 2.96 g (59.8%) of 4-[[4-[(2,6-dichlorophenyl)methyl]-6-(hydroxyamino)-1, 3,5-triazin-2-yl]amino]benzonitrile monohydrochloride monohydrate (compound 21).

b) Compound (21) (0.00227 mol) was stirred in ethylacetate (50 ml). The mixture was washed with NaHCO$_3$ (50 ml saturated solution), then washed with brine, dried, filtered and the solvent was evaporated. The residue was crystallized from methanol, filtered off and dried, yielding 0.60 g (70.6%) of 4-[[4-[(2,6-dichlorophenyl)methyl]-6-(hydroxyamino)-1,3, 5-triazin-2-yl]amino]benzonitrile (compound 33).

EXAMPLE B.7

A mixture of intermediate (30) (0.068 mol) and 4-amino-benzonitrile (0.0420 mol) in 1,4-dioxane (100 ml) was stirred and refluxed for 16 hours under argon. The hot reaction mixture was filtered, and the resulting filtrate was concentrated. The residue was dissolved in DCM (30 ml). The precipitate was filtered off and recrystallized from ACN (250 ml). After cooling to RT, the filtrate was concentrated. The residue was partitioned between DCM/NaOH (3 N). The resulting solution was dried over K$_2$CO$_3$, filtered, and the solvent was evaporated. The residue was recrystallized from CH$_3$OH. The precipitate was filtered off and dried, yielding 1.00 g (5.0%) of N',N-[6-[(2,6-dichlorophenyl)methyl]1,3,5-triazin-2,4-diyl]bis[4-aminobenzonitrile](compound 11).

EXAMPLE B.8 a) DMF (9.0 ml) and intermediate (31) (0.00295 mol) were added to sodium hydride (0.00354 mol) under argon. The reaction mixture was stirred for 10 minutes before adding 4-fluorobenzonitrile (0.00301 mol) and was heated at 80° C. for 3.5 hours. After cooling to RT, the reaction mixture was quenched with H$_2$O. The precipitate was filtered off, dried and purified by flash column chromatography over silica gel (eluent: DCM). The desired fractions were collected and the solvent was evaporated, yielding 4-[4-[(2,6-dichlorophenyl) methyl]-6-(dimethylamino)-1,3,5-triazin-2-yl]amino]-enzonitrile (compound 10).

b) Intermediate (31) (0.00671 mol), dimethylacetamide (20 ml), 4-fluorobenzonitrile (0.01007 mol), and K$_2$CO$_3$ (0.02685 mol) were combined and refluxed for 4 hours under argon. The reaction mixture was stirred and refluxed overnight and was quenched with water and extracted with DCM. The separated organic layer was washed with brine, dried, filtered, and the solvent was evaporated. The residue was purified by flash column chromatography (eluent: DCM). The desired fractions were collected and the solvent was evaporated. The residue was crystallized from CH₃OH, recrystallized from ACN and finally treated with CH₃OH. The precipitate was filtered off and dried, yielding 0.32 g of 4,4'-[[4-[(2,6-dichlorophenyl)methyl]-6-(dimethylamino)-1,3,5-triazin-2-yl]imino]bisbenzonitrile (compound 38).

EXAMPLE B.9

A solution of sodium hydride (0.00195 mol) in DMF (7 ml) was added to compound (1) (0.00186 mol) and the resulting solution was stirred for 5 minutes under argon. Then, chloroacetic acid methyl ester (0.0186 mol) was added and the reaction mixture was heated to 70° C. for 19 hours. The reaction mixture was then quenched with water and the resulting solid was filtered off. The residue was treated with hot ACN, then filtered while still hot. The residue from the cooled filtrate was recrystallized from 1,4-dioxane. The precipitate was filtered off, yielding 0.16 g (19.4%) of methyl N-(4-cyanophenyl)-N-[4-amino-6-[(2,6-dichlorophenyl)methyl]-1,3,5-triazin-2-yl]glycine (compound 39).

EXAMPLE B.10

Sodium hydride (0.00150 mol), ACN (5 ml), compound (1) (0.00135 mol) in 1,4-dioxane (10 ml), and ACN (10 ml) were combined under argon. The solution was stirred for 1 hour. 1-chloro-3-isocyanato-propane (0.00137 mol) was added. The reaction mixture was stirred for 1 hour. 1-methyl-pyrrolidinone (10 ml) was added. The reaction mixture was stirred for 16 hours. Then, the mixture was concentrated. The concentrate was partitioned between DCM/H₂O. The resulting solution was filtered, dried over K₂CO₃, filtered, concentrated and the residue was treated with NH₃ in 1,4-dioxane (12 ml, 0.5 M) and heated under pressure at 55° C. The resulting solution was concentrated and further purified by flash column chromatography (eluent: DCM/CH₃OH 95/5). The pure fractions were collected and the solvent was evaporated, yielding 0.12 g (18.9%) of N-[3-[[4-[(4-cyanophenyl)amino]-6-[(2,6-dichlorophenyl)methyl]-1,3,5-triazin-2-yl]amino]propyl]urea (compound 23).

EXAMPLE B.11

NaOH (0.0128 mol), 1,4-dioxane (5 ml), and guanidine (0.0128 mol) were combined and stirred at RT for 5 minutes under argon. Then, intermediate (27) (0.00128 mol) was added and the reaction mixture was stirred at RT for 16 hours. The reaction mixture was quenched with H₂O, and stirred. The resulting precipitate was filtered off and the residue was stirred in refluxing methanol, cooled, and filtered, yielding 0.34 g (64.3%) of N-[4-[(4-cyanophenyl)amino]-6-[(2,6-dichlorophenyl)methyl]-1,3,5-triazin-2-yl]-guanidine (compound 20).

EXAMPLE B.12

A mixture of intermediate (27) (0.00256 mol) and 3-amino-1,2-propanediol (0.00563 mol) in 1,4-dioxane (10 ml) and 1-methyl-pyrrolidinone (2 ml) was stirred at RT for 48 hours under argon. The reaction mixture was concentrated, quenched with DCM/H₂O and stirred. The precipitate was filtered off, yielding 1.12 g (86.9%) of (±)-4-[[4-[(2,6-dichlorophenyl)methyl]-6-[(2,3-dihydroxypropyl)amino]-1,3,5-triazin-2-yl]amino]benzonitrile (compound 26).

EXAMPLE B.13

Compound (1) (0.0016 mol) and 1,1-dimethoxy-N,N-dimethylmethanamine (21 ml) were combined and stirred vigorously at ambient temperature for 8 hours. The reaction mixture was filtered and the collected solid was washed with ether (Fraction A). Additional compound was obtained by concentration of the filtrate (Fraction B). Fractions A and B were combined and recrystallized from ethanol, yielding 0.15 g of 4-[[4-[(2,6-dichlorophenyl)methyl]-6-[[(dimethylamino)methylene]amino]-1,3,5-triazin-2-yl]amino]benzonitrile (compound 62).

EXAMPLE B.14

A solution of compound (13) (0.000519 mol), LiOH.H₂O (0.000571 mol), methanol (5.0 ml) and H₂O (5.0 ml) was stirred at RT for 16 hours under argon. The reaction mixture was concentrated, redissolved in H₂O, acidified with 1.0 N HCl (0.52 ml), and stirred for 3 days. Then, the solution was filtered, an excess of 1 N HCl and CH₃OH was added to the filtrate, and the solution was stirred for 16 hours. The resulting precipitate was filtered off and dried, yielding 0.18 g (72.7%) of N-[4-[(4-cyanophenyl)-amino]-6-[(2,6-dichlorophenyl)methyl]-1,3,5-triazin-2-yl]glycine (compound 16).

EXAMPLE B.15

A mixture of compound (32) (0.00378 mol) in NH₃ in dioxane (50 ml) was heated in a pressure vessel at 85° C. for 9 days. The solvent was evaporated and the resulting residue was partitioned between DCM/H₂O. The organic layer was filtered, washed with ethanol and concentrated to t 25 ml and filtered, yielding 0.54 g (30.3%) of (±)-2-[[4-[(4-cyanophenyl)amino]-6-[(2,6-dichlorophenyl)amino]-6-[(2,6-dichlorophenyl)methyl]-1,3,5-triazin-2-yl]amino-4-hydroxybutanamide (compound 34).

EXAMPLE B.16

A solution of intermediate (27) in dimethylsulfoxide was treated with NaN₃ in one portion and was stirred at RT for 28 hours. The reaction mixture was poured into ice and then filtered. The precipitate was washed with cold water and was recrystallized from ACN, yielding 0.46 g of 4-[[4-azido-6-[(2,6-dichlorophenyl)methyl]-1,3,5-triazin-2-yl]amino]benzonitrile (compound 68).

Tables 2 to 5 list the compounds that were prepared according to one of the above Examples.

TABLE 2

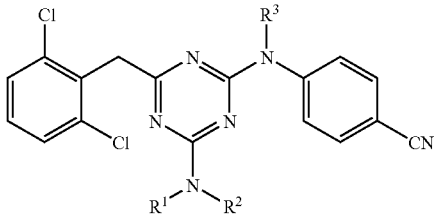

| Co. No. | Ex. No. | R¹ | R² | R³ | salt form |
|---|---|---|---|---|---|
| 1 | B.1a | H | H | H | |
| 6 | B.3 | H | C(=O)N(CH₃)₂ | H | |
| 7 | B.4 | H | CH₃ | H | |
| 10 | B.8a | CH₃ | CH₃ | H | |
| 11 | B.7 | H |  | H | |
| 12 | B.5a | CH₂CH₃ | CH₂CH₃ | H | |
| 13 | B.5a | H | CH₂C(=O)OCH₃ | H | |
| 14 | B.5a | H | CH₂C(=O)NH₂ | H | |
| 15 | B.5b | H | NH₂ | H | |
| 16 | B14 | H | CH₂C(=O)OH | H | |

| Co. No. | Ex. No. | R¹ | R² | R³ | saltform/ stereochem. |
|---|---|---|---|---|---|
| 17 | B.5a | H | 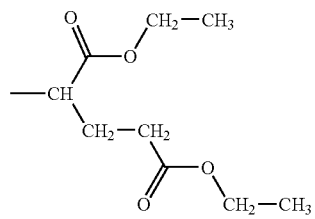 | H | (S) form |
| 18 | B.5b | H | (CH₂)₂OH | H | |
| 19 | B.5b | H | (CH₂)₂NH₂ | H | |
| 20 | B11 | H | 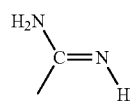 | H | |
| 21 | B.5b B.6a | H | OH | H | HCl.H₂O |
| 22 | B.1b | H | C(=O)CH₃ | H | |
| 23 | B.10 | H | (CH₂)₃NHC(=O)NH₂ | H | |
| 24 | B.5b | H | (CH₂)₄OH | H | |
| 25 | B.5b | H | (CH₂)₃OH | H | |
| 26 | B12 | H | CH₂CH(OH)CH₂OH | H | |
| 27 | B.5b | H | (CH₂)₂O(CH₂)₂OH | H | |
| 28 | B11 | H | 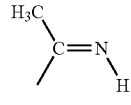 | H | |
| 29 | B.5b | H | (CH₂)₂N(CH₃)₂ | H | |
| 30 | B.5b | H | (CH₂)₃NH₂ | H | |
| 31 | B.5b | H | (CH₂)₃N(CH₃)₂ | H | |
| 32 | B.5a | H | 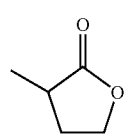 | H | |

TABLE 2-continued

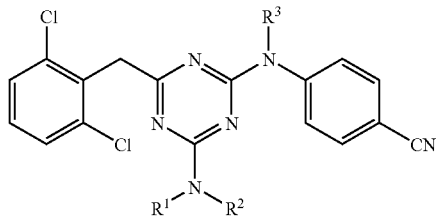

| Co. No. | Ex. No. | R¹ | R² | R³ |
|---|---|---|---|---|
| 33 | B.5b B.6b | H | OH | H |
| 34 | B15 | H | CH(CH₃)CH₂OH-C(=O)NH₂ | H |
| 35 | B.5b | H | CH₂CH₂-(2-thienyl) | H |
| 36 | B11 | H | OCH₃ | H |
| 37 | B.1b | H | C(=O)OCH₂CH₃ | H |
| 38 | B.8b | CH₃ | CH₃ | 4-cyanophenyl |
| 39 | B.9 | H | H | —CH₂C(=O)OCH₃ |

| Co. No. | Ex. No. | R¹ | R² | R³ | salt form |
|---|---|---|---|---|---|
| 40 | B.1b | H | C(=O)CH₃ | —C(=O)CH₃ | |
| 41 | B.1b | C(=O)OCH₂CH₃ | C(=O)OCH₂CH₃ | —C(=O)OCH₂CH₃ | |
| 42 | B.1b | C(=O)CH₃ | C(=O)CH₃ | —C(=O)CH₃ | |
| 43 | B.1b | H | C(=O)OCH₂CH₃ | —C(=O)OCH₂CH₃ | |

TABLE 3

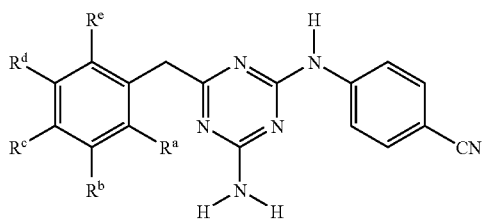

| Co. No. | Ex. No. | Rᵃ | Rᵇ | Rᶜ | Rᵈ | Rᵉ |
|---|---|---|---|---|---|---|
| 2 | B.1a | H | H | H | H | H |
| 3 | B.1a | H | H | H | H | Cl |
| 44 | B.1a | Cl | H | H | Cl | Cl |
| 45 | B.1a | H | H | H | OCF₃ | H |
| 46 | B.1a | H | OCH₃ | H | H | OCH₃ |
| 47 | B.1a | H | H | H | OCH₃ | H |
| 48 | B.1a | H | H | H | OCH₂CH₃ | H |
| 49 | B.1a | H | CH₃ | H | H | CH₃ |
| 50 | B.1a | H | H | H | OCH₃ | OCH₃ |
| 51 | B.1a | H | F | H | H | F |
| 52 | B.1a | F | F | H | H | F |
| 53 | B.1a | H | OCH₃ | H | OCH₃ | H |
| 54 | B.1a | CH₃ | CH₃ | H | CH₃ | CH₃ |

TABLE 3-continued

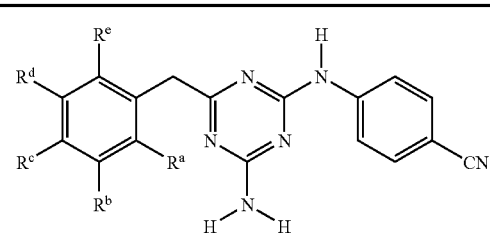

| Co. No. | Ex. No. | Rᵃ | Rᵇ | Rᶜ | Rᵈ | Rᵉ |
|---|---|---|---|---|---|---|
| 55 | B.1a | H | Br | H | H | OCH₃ |
| 56 | B.1a | H | CF₃ | H | H | CF₃ |
| 57 | B.1a | H | CH₃ | H | H | CH₃ |
| 58 | B.1a | F | H | H | H | CF₃ |
| 59 | B.1a | H | F | H | F | H |
| 60 | B.1a | H | C(=O)CH₃ | H | H | OCH₃ |
| 66 | B.5b | H | H | Cl | H | Cl |
| 67 | B.5b | H | H | F | H | Cl |

TABLE 4

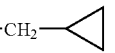

| Co. No. | Ex. No. | R | NR¹R² | R$^a$ | R$^c$ | R$^5$ | R$^6$ | salt form |
|---|---|---|---|---|---|---|---|---|
| 4 | B.1a | H | NH$_2$ | Cl | H | CN | H | |
| 5 | B.1a | H | NH$_2$ | Cl | H | H | Cl | |
| 61 | B.1a | —CH$_2$—⟨cyclopropyl⟩ | NH$_2$ | Cl | H | H | CN | HCl.C$_2$H$_5$OH |
| 62 | B13 | H | N=CH—N(CH$_3$)$_2$ | Cl | H | | | |
| 68 | B.16 | H | N$_3$ | Cl | H | H | CN | |
| 69 | B.6a | H | NHOH | H | Cl | H | CN | |
| 70 | B.6a | H | NHOH | H | F | H | CN | |

TABLE 5

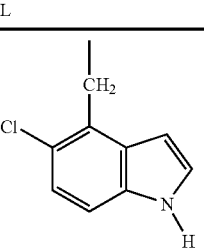

| Co. No. | Ex. No. | L | R$^6$ |
|---|---|---|---|
| 8 | B.2 | (5-chloro-1H-indol-4-yl)methyl | —CN |
| 9 | B.2 | (5-chloro-1H-indol-4-yl)methyl | —CONH$_2$ |
| 63 | | (CH$_2$)$_2$CH=C(CH$_3$)$_2$ | CN |
| 64 | | CH$_2$CH=C(CH$_3$)$_2$ | CN |
| 65 | | (CH$_2$)$_2$CH=C(C$_2$H$_5$)$_2$ | CN |

C. Pharmacological Example

EXAMPLE C.1

A rapid, sensitive and automated assay procedure was used for the in vitro evaluation of anti-HIV agents. An HIV-1 transformed T4-cell line, MT4, which was previously shown (Koyanagi et al., *Int. J. Cancer*, 36, 445-451, 1985) to be highly susceptible to and permissive for HIV infection, served as the target cell line. Inhibition of the HIV-induced cytopathic effect was used as the end point. The viability of both HIV- and mock-infected cells was assessed spectrophotometrically via the in situ reduction of 3-(4,5-dimethylthiazol-2-yl)-2,5-diphenyltetrazolium bromide (MTT). The 50% cytotoxic concentration (CC$_{50}$ in μM) was defined as the concentration of compound that reduced the absorbance of the mock-infected control sample by 50%. The percent protection achieved by the compound in HIV-infected cells was calculated by the following formula:

$$\frac{(OD_T)_{HIV} - (OD_C)_{HIV}}{(OD_C)_{MOCK} - (OD_C)_{HIV}} \text{ expressed in \%,}$$

whereby $(OD_T)_{HIV}$ is the optical density measured with a given concentration of the test compound in HIV-infected cells; $(OD_C)_{HIV}$ is the optical density measured for the control untreated HIV-infected cells; $(OD_C)_{MOCK}$ is the optical density measured for the control untreated mock-infected cells; all optical density values were determined at 540 nm. The dose achieving 50% protection according to the above formula was defined as the 50% inhibitory concentration (IC$_{50}$ in μM). The ratio of CC$_{50}$ to IC$_{50}$ was defined as the selectivity index (SI). The compounds of formula (I) were shown to inhibit HIV-1 effectively. Particular IC$_{50}$, CC$_{50}$ and SI values are listed in Table 6 hereinbelow; the numbers between brackets in the columns "IC$_{50}$ (μM)" and "CC$_{50}$ (μM)" list the number of experiments used to calculate the mean IC$_{50}$ and CC$_{50}$ values.

TABLE 6

| Co. No. | IC$_{50}$ (μM) | CC$_{50}$ (μM) | SI |
|---|---|---|---|
| 1 | 0.002 (96) | >100 (200) | >42553 |
| 2 | 0.29 (10) | >100 (59) | >350 |
| 3 | 0.013 (12) | 51.6 (74) | 3972 |
| 4 | 0.24 (10) | 53.6 (59) | 224 |
| 5 | 0.017 (13) | 47.5 (71) | 2793 |
| 6 | 0.380 (6) | >100 (30) | >263 |
| 7 | 0.01 (11) | >100 (53) | >14285 |

TABLE 6-continued

| Co. No. | IC$_{50}$ (μM) | CC$_{50}$ (μM) | SI |
|---|---|---|---|
| 8 | 0.3 (28) | 14.4 (122) | 4806 |
| 9 | 0.066 (12) | 54.4 (60) | 830 |
| 10 | 0.17 (5) | >100 (32) | >602 |
| 11 | >10.4 (4) | 6.0 (17) | <1 |
| 12 | 8.1 (4) | >20 (1) | >2 |
| 13 | 0.11 (6) | >20 (1) | >178 |
| 14 | 0.031 (5) | 9.1 (1) | 293 |
| 15 | 0.061 (7) | 44.6 (6) | 732 |
| 16 | 2.8 (9) | 79.9 (6) | 28 |
| 17 | 4.3 (4) | >20 (2) | >4 |
| 18 | 0.001 (4) | >20 (2) | >2030 |
| 19 | 0.013 (3) | 10.4 (1) | 810 |
| 20 | >100 (5) | 4.3 (2) | <1 |
| 21 | 0.002 (18) | 8.9 (11) | 4924 |
| 22 | 0.014 (7) | >100 (7) | >6993 |
| 23 | 0.34 (3) | 36.7 (2) | 106 |
| 24 | 0.068 (3) | 36.1 (2) | 529 |
| 25 | 0.029 (3) | 51.6 (2) | 1773 |
| 26 | 0.068 (3) | 59.7 (2) | 883 |
| 27 | 0.056 (2) | 46.8 (2) | 837 |
| 28 | 0.003 (3) | >100 (1) | >37037 |
| 29 | 0.005 (3) | 8.7 (1) | 1741 |
| 30 | 0.04 (3) | 16.5 (1) | 416 |
| 31 | 0.019 (2) | 9.6 (1) | 506 |
| 32 | 2.0 (1) | 83.4 (2) | 42 |
| 33 | 0.002 (4) | 14.1 (2) | 6272 |
| 34 | 0.057 (3) | 42.3 (2) | 746 |
| 35 | 0.70 (3) | 53.0 (2) | 75 |
| 36 | 0.005 (4) | 40.9 (2) | 8097 |
| 37 | 0.011 (4) | 85.0 (2) | 7948 |
| 38 | >100 (3) | >100 (11) | — |
| 39 | 0.078 (5) | >20 (1) | >256 |
| 40 | 0.002 (4) | >100 (2) | >41666 |
| 41 | 0.013 (4) | 40.2 (2) | 3125 |
| 44 | 0.003 (16) | >100 (63) | >35087 |
| 45 | 0.43 (2) | >100 (2) | >233 |
| 46 | 0.040 (3) | >100 (1) | >2506 |
| 47 | 0.082 (6) | >20 (1) | >243 |
| 48 | 0.074 (6) | >20 (1) | >269 |
| 49 | 0.091 (6) | >20 (1) | >220 |
| 50 | 0.079 (4) | >20 (1) | >252 |
| 51 | 0.031 (4) | >20 (1) | >640 |
| 52 | 0.003 (4) | — | >220 |
| 53 | 0.41 (6) | >20 (1) | >48 |
| 54 | 0.005 (9) | 43.8 (6) | 9515 |
| 55 | 0.052 (10) | >20 (7) | >384 |
| 56 | >74.4 (9) | >100 (7) | — |
| 57 | 0.003 (9) | 36.8 (6) | 11883 |
| 58 | 0.014 (8) | 20 (6) | 1418 |
| 59 | 0.42 (6) | >100 (4) | >241 |
| 60 | 0.039 (8) | 71.4 (7) | 1841 |
| 61 | 6.9 (9) | 53.4 (8) | 7 |
| 62 | 0.002 (9) | >100 (7) | >41666 |

D. Composition Examples

The following formulations exemplify typical pharmaceutical compositions suitable for systemic or topical administration to animal and human subjects in accordance with the present invention.

"Active ingredient" (A.I.) as used throughout these examples relates to a compound of formula (I) or a pharmaceutically acceptable addition salt thereof.

EXAMPLE D.1

Film-Coated Tablets

Preparation of Tablet Core

A mixture of 100 g of the A.I., 570 g lactose and 200 g starch was mixed well and thereafter humidified with a solution of 5 g sodium dodecyl sulfate and 10 g polyvinyl-pyrrolidone in about 200 ml of water. The wet powder mixture was sieved, dried and sieved again. Then there was added 100 g microcrystalline cellulose and 15 g hydrogenated vegetable oil. The whole was mixed well and compressed into tablets, giving 10.000 tablets, each comprising 10 mg of the active ingredient.

Coating

To a solution of 10 g methyl cellulose in 75 ml of denaturated ethanol there was added a solution of 5 g of ethyl cellulose in 150 ml of dichloromethane. Then there were added 75 ml of dichloromethane and 2.5 ml 1,2,3-propanetriol. 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated color suspension and the whole was homogenated. The tablet cores were coated with the thus obtained mixture in a coating apparatus.

The invention claimed is:

1. A method for preparing a compound of formula (I-a),

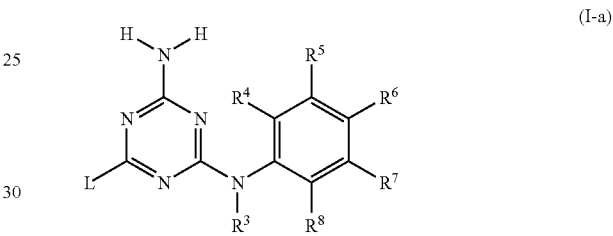

(I-a)

wherein

R$^3$ is hydrogen, Ar$^1$, C$_{1-6}$alkylcarbonyl, C$_{1-6}$alkyl, C$_{1-6}$alkyloxycarbonyl, C$_{1-6}$alkyl substituted with C$_{1-6}$alkyloxycarbonyl; and R$^4$, R$^5$, R$^6$, R$^7$ and R$^8$ are each independently selected from hydrogen, hydroxy, halo, C$_{1-6}$alkyl, C$_{1-6}$alkyloxy, cyano, aminocarbonyl, nitro, amino, trihalomethyl or trihalomethyloxy;

L is C$_{1-10}$alkyl; C$_{3-10}$alkenyl; C$_{3-10}$alkynyl; C$_{3-7}$cycloalkyl; or L is C$_{1-10}$alkyl substituted with one or two substituents independently selected from C$_{3-7}$cycloalkyl; indolyl or indolyl substituted with one, two, three or four substituents each independently selected from halo, C$_{1-6}$alkyl, C$_{1-6}$alkyloxy, cyano, aminocarbonyl, nitro, amino, trihalomethyl, trihalomethyloxy, C$_{1-6}$alkylcarbonyl; phenyl or phenyl substituted with one, two, three, four or five substituents each independently selected from halo, hydroxy, C$_{1-6}$alkyl, C$_{1-6}$alkyloxy, cyano, aminocarbonyl, nitro, amino, trihalomethyl, trihalomethyloxy, C$_{1-6}$alkylcarbonyl; and, Ar$^1$ is phenyl, or phenyl substituted with one, two or three substituents each independently selected from halo, C$_{1-6}$alkyl, C$_{1-6}$alkyloxy, cyano, nitro or trifluoromethyl; with the proviso that the following compounds

| Co. No. | L | R$^3$ | R$^4$ | R$^5$ | R$^6$ | R$^7$ | R$^8$ |
|---|---|---|---|---|---|---|---|
| a | 1-(4-(2-methylpropyl)-phenyl)ethyl | H | CH$_3$ | H | H | H | H |
| b | 1-(4-(2-methylpropyl)-phenyl)ethyl | H | H | H | NO$_2$ | H | H |

-continued

| Co. No. | L | R³ | R⁴ | R⁵ | R⁶ | R⁷ | R⁸ |
|---|---|---|---|---|---|---|---|
| c | 1-(4-(2-methylpropyl)-phenyl)ethyl | C₆H₅ | H | H | H | H | H |
| d | 1-(4-(2-methylpropyl)-phenyl)ethyl | H | NO₂ | H | CH₃ | H | H |
| e | 1-(4-(2-methylpropyl)-phenyl)ethyl | H | H | H | NH₂ | H | H |
| f | 4-(2-methylpropyl)-phenylmethyl | H | H | CF₃ | H | H | H |
| g | 1-(4-(2-methylpropyl)-phenyl)ethyl | H | H | H | Cl | H | H |
| h | 4-(2-methylpropyl)-phenylmethyl | H | H | H | H | H | H |
| i | 3,4-dimethoxyphenyl-methyl | H | H | H | H | H | H |
| j | 2,3-dimethoxyphenyl-methyl | H | H | H | H | H | H |
| k | 3,4-diethoxyphenyl-methyl | H | H | H | H | H | H |
| l | 2-(3,5-(1,1-dimethyl-ethyl)-4-hydroxy-phenyl)ethyl | H | H | H | H | H | H |
| m | 2-(3,5-(1,1-dimethyl-ethyl)-4-hydroxy-phenyl)ethyl | H | H | t-Bu | OH | t-Bu | H |
| n | phenylmethyl | H | CH₃ | H | H | H | H |
| o | phenylmethyl | H | H | H | H | H | H | are not included, comprising the step of reacting an intermediate of formula (II),

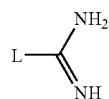

wherein
- L is $C_{1-10}$alkyl; $C_{3-10}$alkenyl; $C_{3-10}$alkynyl; $C_{3-7}$cycloalkyl; or
- L is $C_{1-10}$alkyl substituted with one or two substituents independently selected from $C_{3-7}$cycloalkyl; indolyl or indolyl substituted with one, two, three or four substituents each independently selected from halo, $C_{1-6}$alkyl, $C_{1-6}$alkyloxy, cyano, aminocarbonyl, nitro, amino, trihalomethyl, trihalomethyloxy, $C_{1-6}$alkylcarbonyl; phenyl or phenyl substituted with one, two, three, four or five substituents each independently selected from halo, hydroxy, $C_{1-6}$alkyl, $C_{1-6}$alkyloxy, cyano, aminocarbonyl, nitro, amino, trihalomethyl, trihalomethyloxy, $C_{1-6}$alkylcarbonyl;

with an intermediate of formula (III),

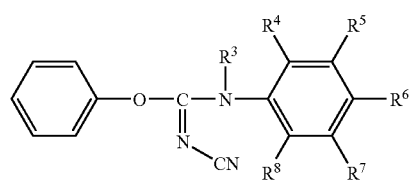

wherein
- $R^3$ is hydrogen, $Ar^1$, $C_{1-6}$alkylcarbonyl, $C_{1-6}$alkyl, $C_{1-6}$alkyloxycarbonyl, $C_{1-6}$alkyl substituted with $C_{1-6}$alkyloxycarbonyl; and
- $R^4$, $R^5$, $R^6$, $R^7$ and $R^8$ are each independently selected from hydrogen, hydroxy, halo, $C_{1-6}$alkyl, $C_{1-6}$alkyloxy, cyano, aminocarbonyl, nitro, amino, trihalomethyl or trihalomethyloxy; and,
- $Ar^1$ is phenyl, or phenyl substituted with one, two or three substituents each independently selected from halo, $C_{1-6}$alkyl, $C_{1-6}$alkyloxy, cyano, nitro or trifluoromethyl;

in a reaction-inert solvent.

2. A method for preparing a compound of formula (I-a),

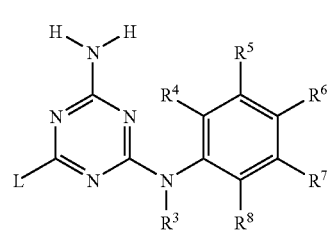

wherein
- $R^3$ is hydrogen, $Ar^1$, $C_{1-6}$alkylcarbonyl, $C_{1-6}$alkyl, $C_{1-6}$alkyloxycarbonyl, $C_{1-6}$alkyl substituted with $C_{1-6}$alkyloxycarbonyl; and
- $R^4$, $R^5$, $R^7$ and $R^8$ are each independently selected from hydrogen, hydroxy, halo, $C_{1-6}$alkyl, $C_{1-6}$alkyloxy, cyano, aminocarbonyl, nitro, amino, trihalomethyl or trihalomethyloxy;
- $R^6$ is selected from the group consisting of cyano and aminocarbonyl;
- L is $C_{1-10}$alkyl; $C_{3-10}$alkenyl; $C_{3-10}$alkynyl; $C_{3-7}$cycloalkyl; or
- L is $C_{1-10}$alkyl substituted with one or two substituents independently selected from $C_{3-7}$cycloalkyl; indolyl or indolyl substituted with one, two, three or four substituents each independently selected from halo, $C_{1-6}$alkyl, $C_{1-6}$alkyloxy, cyano, aminocarbonyl, nitro, amino, trihalomethyl, trihalomethyloxy, $C_{1-6}$alkylcarbonyl; phenyl or phenyl substituted with one, two, three, four or five substituents each independently selected from halo, hydroxy, $C_{1-6}$alkyl, $C_{1-6}$alkyloxy, cyano, aminocarbonyl, nitro, amino, trihalomethyl, trihalomethyloxy, $C_{1-6}$alkylcarbonyl; and,
- $Ar^1$ is phenyl, or phenyl substituted with one, two or three substituents each independently selected from halo, $C_{1-6}$alkyl, $C_{1-6}$alkyloxy, cyano, nitro or trifluoromethyl;

comprising the step of reacting an intermediate of formula (II),

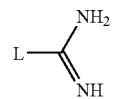

wherein
- L is $C_{1-10}$alkyl; $C_{3-10}$alkenyl; $C_{3-10}$alkynyl; $C_{3-7}$cycloalkyl; or
- L is $C_{1-10}$alkyl substituted with one or two substituents independently selected from $C_{3-7}$cycloalkyl; indolyl or indolyl substituted with one, two, three or four substituents each independently selected from halo, $C_{1-6}$alkyl, $C_{1-6}$alkyloxy, cyano, aminocarbonyl, nitro, amino, trihalomethyl, trihalomethyloxy, $C_{1-6}$alkylcarbonyl; phenyl or phenyl substituted with one, two, three, four or five substituents each independently selected from halo, hydroxy, $C_{1-6}$alkyl, $C_{1-6}$alkyloxy, cyano, aminocarbonyl, nitro, amino, trihalomethyl, trihalomethyloxy, $C_{1-6}$alkylcarbonyl;

with an intermediate of formula (III),

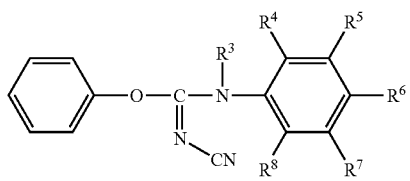

(III)

wherein
  $R^3$ is hydrogen, $Ar^1$, $C_{1-6}$alkylcarbonyl, $C_{1-6}$alkyl, $C_{1-6}$alkyloxycarbonyl, $C_{1-6}$alkyl substituted with $C_{1-6}$alkyloxycarbonyl; and
  $R^4$, $R^5$, $R^7$ and $R^8$ are each independently selected from hydrogen, hydroxy, halo, $C_{1-6}$alkyl, $C_{1-6}$alkyloxy, cyano, aminocarbonyl, nitro, amino, trihalomethyl or trihalomethyloxy;
  $R^6$ is selected from the group consisting of cyano and aminocarbonyl; and, $Ar^1$ is phenyl, or phenyl substituted with one, two or three substituents each independently selected from halo, $C_{1-6}$alkyl, $C_{1-6}$alkyloxy, cyano, nitro or trifluoromethyl;
  in a reaction-inert solvent.

3. A process for preparing 4-[[4-amino-6-[(2,6-dichlorophenyl)methyl]-1,3,5-triazin-2-yl]amino]benzonitrile comprising the step of reacting 2,6-dichlorobenzeneethanimidamide with phenyl N'-cyano-N-(4-cyanophenyl)-carbamimidate in a reaction-inert solvent.

* * * * *